United States Patent [19]
Devine et al.

[11] Patent Number: 5,962,688
[45] Date of Patent: Oct. 5, 1999

[54] STEREOSELECTIVE DEOXYGENATION REACTION

[75] Inventors: Paul N. Devine, Lincroft; Ulf H. Dolling, Westfield; Lisa F. Frey, Somerset; Richard D. Tillyer, Westfield; David M. Tschaen, Holmdel, all of N.J.; Yoshiaki Kato, Okazaki, Japan

[73] Assignees: Merck & Co., Inc., Rahway, N.J.; Banyu Pharmaceutical Co., Ltd., Tokyo, Japan

[21] Appl. No.: 08/907,449

[22] Filed: Aug. 8, 1997

Related U.S. Application Data

[60] Provisional application No. 60/023,614, Aug. 9, 1996, and provisional application No. 60/028,438, Oct. 10, 1996.

[51] Int. Cl.[6] .................. C07D 221/04; C07D 317/60; C07C 69/753; C07C 67/00

[52] U.S. Cl. ................. 546/112; 549/447; 560/56; 560/80; 562/451

[58] Field of Search .................. 546/112; 549/447; 560/56, 80; 562/451

[56] References Cited

U.S. PATENT DOCUMENTS 5,716,984   2/1998   Cousins et al. .................. 514/447

*Primary Examiner*—Bernard Dentz
*Attorney, Agent, or Firm*—Valerie J. Camara; Mark R. Daniel

[57] ABSTRACT

This invention relates to a key intermediate in the synthesis of an endothelin antagonist, the synthesis of this key intermediate and the synthesis of an endothelin antagonist using this intermediate in a stereoselective deoxygenation reaction.

23 Claims, No Drawings

STEREOSELECTIVE DEOXYGENATION REACTION

This application claims priority under 35 U.S.C. 119 (e) (1) based on verified Provisional Applications 60/023,614 filed Aug. 9, 1996 and 60/028,438 filed Oct. 10, 1996.

BACKGROUND OF THE INVENTION

The present invention relates to novel key intermediates in the synthesis of an endothelin antagonist and the method for preparing these key intermediates of formula I.

Two endothelin receptor subtypes $ET_A$ and $ET_B$ are known so far. The compounds of the present invention possess high affinity to at least one of two receptor subtypes, responsible for the dilation of smooth muscle, such as blood vessels or in the trachea. The endothelin antagonist compounds of the present invention provide a new therapeutic potential, particularly for the treatment of hypertension, pulmonary hypertension, Raynaud's disease, acute renal failure, myocardial infarction, angina pectoris, cerebral infarction, cerebral vasospasm, arteriosclerosis, asthma, gastric ulcer, diabetes, restenosis, prostatauxe endotoxin shock, endotoxin-induced multiple organ failure or disseminated intravascular coagulation, and/or cyclosporin-induced renal failure or hypertension.

Endothelin is a polypeptide composed of amino acids, and it is produced by vascular endothelial cells of human or pig. Endothelin has a potent vasoconstrictor effect and a sustained and potent pressor action (Nature, 332, 411–415 (1988)).

Three endothelin isopeptides (endothelin-1, endothelin-2 and endothelin-3), which resemble one another in structure, exist in the bodies of animals including human, and these peptides have vasoconstriction and pressor effects (Proc. Natl. Acad, Sci, USA, 86, 2863–2867 (1989)).

As reported, the endothelin levels are clearly elevated in the blood of patients with essential hypertension, acute myocardial infarction, pulmonary hypertension, Raynaud's disease, diabetes or atherosclerosis, or in the washing fluids of the respiratory tract or the blood of patients with asthmaticus as compared with normal levels (Japan, J. Hypertension, 12, 79, (1989), J. Vascular medicine Biology, 2, 207 (1990), Diabetologia, 33, 306–310 (1990), J. Am. Med. Association, 264, 2868 (1990), and The Lancet, ii, 747–748 (1989) and ii, 1144–1147 (1990)).

Further, an increased sensitivity of the cerebral blood vessel to endothelin in an experimental model of cerebral vasospasm (Japan. Soc. Cereb. Blood Flow & Metabol., 1, 73 (1989)), an improved renal function by the endothelin antibody in an acute renal failure model (J. Clin, invest., 83, 1762–1767 (1989), and inhibition of gastric ulcer development with an endothelin antibody in a gastric ulcer model (Extract of Japanese Society of Experimental Gastric Ulcer, 50 (1991)) have been reported. Therefore, endothelin is assumed to be one of the mediators causing acute renal failure or cerebral vasospasm following subarachnoid hemorrhage.

Further, endothelin is secreted not only by endothelial cells but also by tracheal epithelial cells or by kidney cells (FEBS Letters, 255, 129–132 (1989), and FEBS Letters, 249, 42–46 (1989)).

Endothelin was also found to control the release of physiologically active endogenous substances such as renin, atrial natriuretic peptide, endothelium-derived relaxing factor (EDRF), thromboxane $A_2$, prostacyclin, noradrenaline, angiotensin II and substance P (Biochem. Biophys. Res. Commun., 157, 1164–1168 (1988); Biochem. Biophys. Res. Commun., 155, 20 167–172 (1989); Proc. Natl. Acad. Sci. USA, 85 1 9797–9800 (1989); J. Cardiovasc. Pharmacol., 13, S89–S92 (1989); Japan. J. Hypertension, 12, 76 (1989) and Neuroscience Letters, 102, 179–184 (1989)). Further, endothelin causes contraction of the smooth muscle of gastrointestinal tract and the uterine smooth muscle (FEBS Letters, 247, 337–340 (1989); Eur. J. Pharmacol., 154, 227–228 (1988); and Biochem. Biophys Res. Commun., 159, 317–323 (1989)). Further, endothelin was found to promote proliferation of rat vascular smooth muscle cells, suggesting a possible relevance to the arterial hypertrophy (Atherosclerosis, 78, 225–228 (1989)). Furthermore, since the endothelin receptors are present in a high density not only in the peripheral tissues but also in the central nervous system, and the cerebral administration of endothelin induces a behavioral change in animals, endothelin is likely to play an important role for controlling nervous functions (Neuroscience Letters, 97, 276–279 (1989)). Particularly, endothelin is suggested to be one of mediators for pain (Life Sciences, 49, PL61–PL65 (1991)).

Internal hyperplastic response was induced by rat carotid artery balloon endothelial denudation. Endothelin causes a significant worsening of the internal hyperplasia (J. Cardiovasc. Pharmacol., 22, 355–359 & 371–373(1993)). These data support a role of endothelin in the phathogenesis of vascular restenosis. Recently, it has been reported that both $ET_A$ and $ET_B$ receptors exist in the human prostate and endothelin produces a potent contraction of it. These results suggest the possibility that endothelin is involved in the pathophysiology of benign prostatic hyperplasia (J. Urology, 151, 763–766(1994), Molecular Pharmocol., 45, 306–311 (1994)).

On the other hand, endotoxin is one of potential candidates to promote the release of endothelin. Remarkable elevation of the endothelin levels in the blood or in the culture supernatant of endothelial cells was observed when endotoxin was exogenously administered to animals or added to the culture endothelial cells, respectively. These findings suggest that endothelin is an important mediator for endotoxin-induced diseases (Biochem. Biophys. Commun., 161, 1220–1227 (1989); and Acta Physiol. Scand., 137, 317–318 (1989)).

Further, it was reported that cyclosporin remarkably increased endothelin secretion in the renal cell culture (LLC-PKL cells) (Eur. J. Pharmacol., 180, 191–192 (1990)). Further, dosing of cyclosporin to rats reduced the glomerular filtration rate and increased the blood pressure in association with a remarkable increase in the circulating endothelin level. This cyclosporin-induced renal failure can be suppressed by the administration of endothelin antibody (Kidney Int., 37, 1487–1491 (1990)). Thus, it is assumed that endothelin is significantly involved in the pathogenesis of the cyclosporin-induced diseases.

Such various effects of endothelin are caused by the binding of endothelin to endothelin receptors widely distributed in many tissues (Am. J. Physiol., 256, R856–R866 (1989)).

It is known that vasoconstriction by the endothelins is caused via at least two subtypes of endothelin receptors (J. Cardiovasc. Pharmacol., 17(Suppl.7), S119–S121 (1991)). One of the endothelin receptors is $ET_A$ receptor Selective to ET-1 rather than ET-3, and the other is $ET_B$ receptor equally active to ET-1 and ET-3. These receptor proteins are reported to be different from each other (Nature, 348, 730–735 (1990)).

These two subtypes of endothelin receptors are differently distributed in tissues. It is known that the $ET_A$ receptor is present mainly in cardiovascular tissues, whereas the $ET_B$ receptor is widely distributed in various tissues such as brain, kidney, lung, heart and vascular tissues.

Substances which specifically inhibit the binding of endothelin to the endothelin receptors are believed to antagonize various pharmacological activities of endothelin and to be useful as a drug in a wide field. Since the action of the endothelins is caused via not only the $ET_A$ receptor but also the $ET_B$ receptor, novel non-peptidic substances with ET receptor antagonistic activity to either receptor subtype are desired to block activities of the endothelins effectively in various diseases.

Endothelin is an endogenous substance which directly or indirectly (by controlling liberation of various endogenous substances) induces sustained contraction or relaxation of vascular or non-vascular smooth muscles, and its excess production or excess secretion is believed to be one of pathogeneses for hypertension, pulmonary hypertension, Raynaud's disease, bronchial asthma, gastric ulcer, diabetes, arteriosclerosis, restenosis, acute renal failure, myocardial infarction, angina pectoris, cerebral vasospasm and cerebral infarction. Further, it is suggested that endothelin serves as an important mediator involved in diseases such as restenosis, prostatauxe, endotoxin shock, endotoxin-induced multiple organ failure or disseminated intravascular coagulation, and cyclosporin-induced renal failure or hypertension. Two endothelin receptors $ET_A$ and $ET_B$ are known so far. An antagonistic agent against the $ET_B$ receptor as well as the $ET_A$ receptor is useful as a drug. In the field of anti-endothelin agents, some non-peptidic compounds possessing antagonistic activity against endothelin receptors were already disclosed in patents (for example, EP 0526708 A1, WO 93/08799 A1). Accordingly, it is an object of the present invention to provide a novel therapeutics for the treatment of the above-mentioned various diseases by an invention of a novel and potent non-peptidic antagonist against either $ET_A$ or $ET_B$ receptor.

In order to accomplish the above object, the present inventors have developed an aldol reaction which enables them to prepare the compound of Formula I,

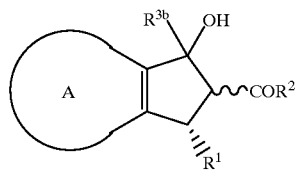

I and use this key intermediate in a stereoselective deoxygenation reaction, also developed by the inventors, to prepare endothelin antagonists of the following structure:

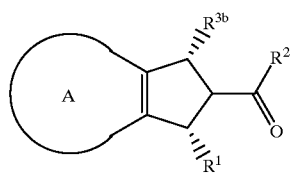

wherein

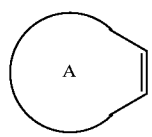

represents: 5- or 6-membered heterocyclyl, 5- or 6-membered carbocyclyl, and aryl;

$R^{3b}$ is aryl, or heteroaryl;
$R^1$ is $C_1$–$C_8$ alkyl, $C_2$–$C_8$ alkenyl, $C_2$–$C_8$ alkynyl, $C_3$–$C_8$ cycloalkyl, aryl, or heteroaryl;
$R^2$ is $OR^4$ and $N(R^5)_2$;
$R^4$ is $C_1$–$C_8$ alkyl; and
$R^5$ is: H, $C_1$–$C_8$ alkyl, or aryl.

SUMMARY OF THE INVENTION

This invention relates to a key intermediate in the synthesis of an endothelin antagonist, the synthesis of this key intermediate and the synthesis of an endothelin antagonist using this intermediate in a stereoselective deoxygenation reaction.

The instant invention relates to a compound of formula I:

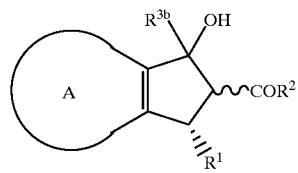

I wherein

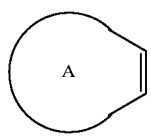

represents:
a) 5- or 6-membered heterocyclyl containing one, two or three double bonds, but at least one double bond and 1, 2 or 3 heteroatoms selected from O, N and S, the heterocyclyl is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$, b) 5- or 6-membered carbocyclyl containing one or two double bonds, but at least one double bond, the carbocyclyl is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$, c) aryl, wherein aryl is as defined below,
$C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, are unsubstituted or substituted with one, two or three substituents selected from the group consisting of: OH, $CO_2R^4$, Br, Cl, F, I, $CF_3$, $N(R^5)2$, $C_1$–$C_8$ alkoxy, $C_3$–$C_8$ cycloalkyl, $CO(CH_2)_nCH_3$, and $CO(CH_2)_nCH_2N(R^5)_2$, aryl is defined as phenyl or naphthyl, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, $CO(CH_2)_nCH_2N(R^5)_2$, and when two substituents are located on adjacent carbons they can join to form a 5- or 6-membered ring with one, two or three heteroatoms selected from O, N, and S, which is unsubstituted or substituted with with one, two or three substituents selected from the group consisting of: H, OH, $CO_2R^6$, Br, Cl, F, I, $CF_3$, $N(R^7)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$, n is 0 to 5;

$R^1$ is:
a) $C_1$–$C_8$ alkyl, $C_2$–$C_8$ alkenyl, $C_2$–$C_8$ alkynyl, $C_3$–$C_8$ cycloalkyl,
b) aryl, or
c) heteroaryl;
  heteroaryl is defined as a 5- or 6-membered aromatic ring containing 1, 2 or 3 heteroatoms selected from O, N and S, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$, $R^2$ is $OR^4$ or $N(R^5)_2$;

$R^{3a}$ is:
a) —CO-$C_1$–$C_8$ alkyl,
b) —CO-aryl, or
c) —CO-heteroaryl;

$R^{3b}$ is:
a) $C_1$–$C_8$ alkyl,
b) aryl, or
c) heteroaryl;

$R^4$ is $C_1$–$C_8$ alkyl; and $R^5$ is: H, $C_1$–$C_8$ alkyl, or aryl.

Also within the scope of the instant invention is a process for the preparation of a compound of formula I:

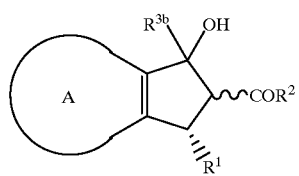

wherein the substituents are as defined above comprising reacting a

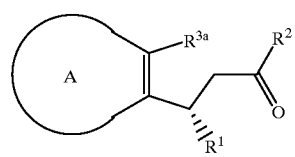

in the presence of a strong base and an aprotic solvent at a temperature range of −78° C. to about 25° C.

Also within the scope of the instant invention is a process for the preparation of a compound of formula II:

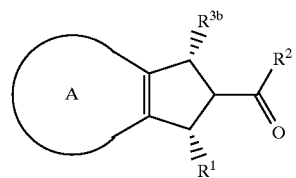

wherein the substituents are as defined above, comprising reacting a compound of formula I

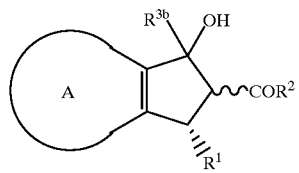

with a reducing agent and an acid in a solvent at a temperature range of about −78° C. to about 100° C.

DETAILED DESCRIPTION OF THE INVENTION

The instant invention relates to a compound of formula I:

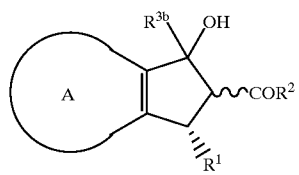

wherein

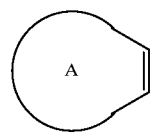

represents:
a) 5- or 6-membered heterocyclyl containing one, two or three double bonds, but at least one double bond and 1, 2 or 3 heteroatoms selected from O, N and S, the heterocyclyl is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$, b) 5- or 6-membered carbocyclyl containing one or two double bonds, but at least one double bond, the carbocyclyl is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$, c) aryl, wherein aryl is as defined below, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, are unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_3$–$C_8$ cycloalkyl, $CO(CH_2)_nCH_3$, and $CO(CH_2)_nCH_2N(R^5)_2$, aryl is defined as phenyl or naphthyl, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, $CO(CH_2)_nCH_2N(R^5)_2$, and when two substituents are located on adjacent carbons they can join to form a 5- or 6-membered ring with one, two or three heteroatoms selected from O, N, and S, which is unsubstituted or substituted with with one, two or three substituents selected from the group consisting of: H, OH, $CO_2R^6$, Br, Cl, F, I, $CF_3$, $N(R^7)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$, n is 0 to 5;

$R^1$ is:
 a) $C_1$–$C_8$ alkyl, $C_2$–$C_8$ alkenyl, $C_2$–$C_8$ alkynyl, $C_3$–$C_8$ cycloalkyl,
 b) aryl, or
 c) heteroaryl;
  heteroaryl is defined as a 5- or 6-membered aromatic ring containing 1, 2 or 3 heteroatoms selected from O, N and S. which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$, $R^2$ is $OR^4$ or $N(R^5)_2$;

$R^{3b}$ is:
 a) $C_1$–$C_8$ alkyl,
 b) aryl, or
 c) heteroaryl;

$R^4$ is $C_1$–$C_8$ alkyl; and $R^5$ is: H, $C_1$–$C_8$ alkyl, or aryl.

An embodiment of the invention is a process for the preparation of a compound of formula I:

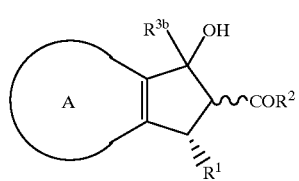

I wherein

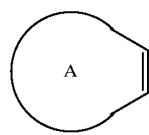

represents:
 a) 5- or 6-membered heterocyclyl containing one, two or three double bonds, but at least one double bond and 1, 2 or 3 heteroatoms selected from O, N and S, the heterocyclyl is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$,
 b) 5- or 6-membered carbocyclyl containing one or two double bonds, but at least one double bond, the carbocyclyl is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$,
 c) aryl, wherein aryl is as defined below,
  $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, are unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_3$–$C_8$ cycloalkyl, $CO(CH_2)_nCH_3$, and $CO(CH_2)_nCH_2N(R^5)_2$,
  aryl is defined as phenyl or naphthyl, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, $CO(CH_2)_nCH_2N(R^5)_2$, and when two substituents are located on adjacent carbons they can join to form a 5- or 6-membered ring with one, two or three heteroatoms selected from O, N, and S, which is unsubstituted or substituted with with one, two or three substituents selected from the group consisting of: H, OH, $CO_2R^6$, Br, Cl, F, I, $CF_3$, $N(R^7)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$, n is 0 to 5;

$R^1$ is:
 a) $C_1$–$C_8$ alkyl, $C_2$–$C_8$ alkenyl, $C_2$–$C_8$ alkynyl, $C_3$–$C_8$ cycloalkyl,
 b) aryl, or
 c) heteroaryl;
  heteroaryl is defined as a 5- or 6-membered aromatic ring containing 1, 2 or 3 heteroatoms selected from O, N and S which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$, $R^2$ is $OR^4$ or $N(R^5)_2$;

$R^{3a}$ is:
  a) —CO-$C_1$–$C_8$ alkyl,
  b) —CO-aryl, or
  c) —CO-heteroaryl;

$R^{3b}$ is:
  a) $C_1$–$C_8$ alkyl,
  b) aryl, or
  c) heteroaryl;

$R^4$ is $C_1$–$C_8$ alkyl; and
$R^5$ is: H, $C_1$–$C_8$ alkyl, or aryl,
comprising reacting a

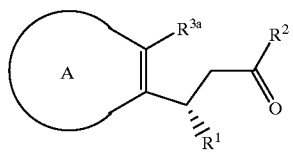

in the presence of a strong base and an aprotic solvent at a temperature range of −78° C. to about 25° C.

The process as recited above, wherein the strong base is selected from the group consisting of: LDA, LiHMDS, KHMDS, NaHMDS, KO$^t$Bu, and sodium t-amylate, in about 2 to about 6 equivalents; the aprotic solvent is selected from the group consisting of tetrahydrofuran, diethyl ether, MTBE (methyl t-butyl ether), benzene, toluene, pentane, hexane, dioxane and a mixture of said solvents; and the temperature range is about −78° C. to about 25° C., and preferably about −50° C. to about 25° C.

The process conditions for the process recited above are wherein the strong base is LiHMDS, KHMDS, or NaHMDS, preferably in about 3 to about 4 equivalents, the aprotic solvent is tetrahydrofuran and the temperature range is preferably about 0° C. to about 25° C.

A second embodiment of the invention is a process for the preparation of a compound of formula II:

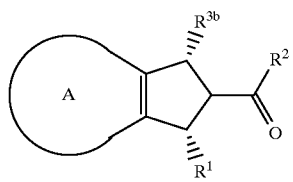

II wherein

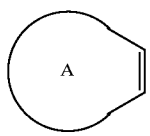

represents:
  a) 5- or 6-membered heterocyclyl containing one, two or three double bonds, but at least one double bond and 1, 2 or 3 heteroatoms selected from O, N and S, the heterocyclyl is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$, b) 5- or 6-membered carbocyclyl containing one or two double bonds, but at least one double bond, the carbocyclyl is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$, c) aryl, wherein aryl is as defined below,
    $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, are unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_3$–$C_8$ cycloalkyl, $CO(CH_2)_nCH_3$, and $CO(CH_2)_nCH_2N(R^5)_2$, aryl is defined as phenyl or naphthyl, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, $CO(CH_2)_nCH_2N(R^5)_2$, and when two substituents are located on adjacent carbons they can join to form a 5- or 6-membered ring with one, two or three heteroatoms selected from O, N, and S, which is unsubstituted or substituted with with one, two or three substituents selected from the group consisting of: H, OH, $CO_2R^6$, Br, Cl, F, I, $CF_3$, $N(R^7)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$, $R^1$ is:
  a) $C_1$–$C_8$ alkyl, $C_2$–$C_8$ alkenyl, $C_2$–$C_8$ alkynyl, $C_3$–$C_8$ cycloalkyl,
  b) aryl, or
  c) heteroaryl;
    heteroaryl is defined as a 5- or 6-membered aromatic ring containing 1, 2 or 3 heteroatoms selected from O, N and S, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$, n is 0 to 5;
$R^2$ is $OR^4$ or $N(R^5)_2$;
$R^{3b}$ is:
  a) $C_1$–$C_8$ alkyl,
  b) aryl, or
  c) heteroaryl;
$R^4$ is $C_1$–$C_8$ alkyl; and
$R^5$ is: H, $C_1$–$C_8$ alkyl, or aryl,
comprising reacting a compound of formula I

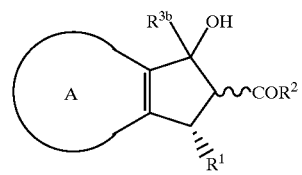

I with a reducing agent and optionally an acid in a solvent at a temperature range of about −78° C. to about 100° C.

The process as recited above, wherein the reducing agent is selected from the group consisting of: a hydride, a borane, $C_5$–$C_6$ cycloalkene with a transition metal catalyst and $H_2$ with a transition metal catalyst. The reducing agents useful in this process in about 2 to about 20 equivalents and preferably about 2 to about 5 equivalents are: hydrides, such as $R_3SiH$, $R_2SiH_2$, wherein R is $C_1$–$C_8$ alkyl or aryl, and $NaBH_4$, boranes, such as $BH_3.NHMe_2$, $BH_3.SMe_2$, $BH_3$.pyridine, and $BH_3$.THF, $C_5$–$C_6$ cycloalkene with a transition metal catalyst, such as cyclohexene or cyclohexadiene with Pd/C, Pt-C, Rh/Al and Raney Ni, $H_2$ with a transition metal catalyst, such as Pd-C, Pt-C, Rh/Al and Raney Ni, or $SmI_2$.

The process as recited above, wherein the acid is a Lewis acid, when the reducing agent is a hydride, a borane or $C_5$–$C_6$ cycloalkene with a transition metal catalyst, a protic acid, when the reducing agent is $H_2$ with a transition metal catalyst, or no acid, when the reducing agent is $SmI_2$. The Lewis acids in about 2 to about 5 equivalents, such as $TiCl_4$, $BF_3$, $BCl_3$, $SnCl_4$, $AlCl_3$, and $TiCl_2(OiPr)_2$ are useful in this process. Protic acids, such as trifluoroacetic acid, HCl, and $H_2SO_4$ are useful in this process.

The process as recited above, wherein the solvent is an aprotic solvent, when the acid is a Lewis acid and the reducing agent is a hydride, a borane or $C_5$–$C_6$ cycloalkene with a transition metal catalyst, a protic solvent, when the acid is a protic acid and the reducing agent is $H_2$ with a transition metal catalyst, or a solvent system consisting of an aprotic solvent and a protic solvent when the reducing agent is $SmI_2$. Aprotic solvents such as tetrahydrofuran, diethyl ether, MTBE (methyl t-butyl ether), dioxane, $CH_2Cl_2$, $CHCl_3$, nitromethane, toluene, and dichlorobenzene, and protic solvents such as ethanol, methanol or isopropanol, are solvents within the scope of the invention.

The process as recited above, wherein temperature range is about −78° C. to about 20° C. and preferably about −20° C. to about 10° C., when the acid is a Lewis acid and the reducing agent is a hydride or a borane, about 0° C. to about 100° C. and preferably about 0° C. to about 40° C., when the acid is a Lewis acid or a protic acid and the reducing agent is a $C_5$–$C_6$ cycloalkene with a transition metal catalyst or $H_2$ with a transition metal catalyst, or about 0° C. to about 30° C., when the reducing agent is $SmI_2$.

The preferred conditions for the process recited above are wherein the hydride is $R_3SiH$, the Lewis acid is $TiCl_4$, the aprotic solvent is nitromethane and the temperature range is about −5° C. to about 5° C.

The process as recited above for the preparation of a compound of formula:

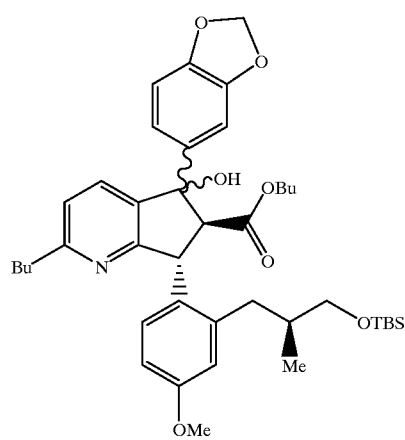

comprising reacting a ketone of formula:

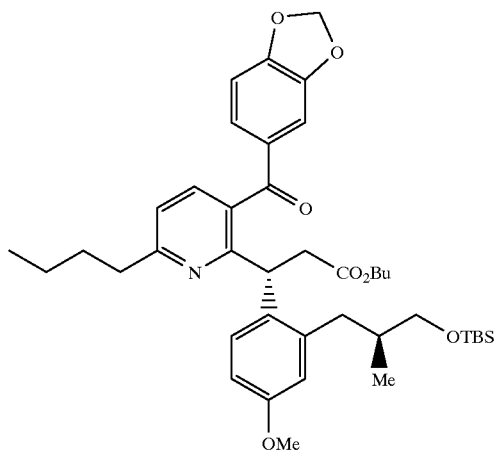

in tetrahydrofuran with about 3 to about 5 equivalents of lithium bis(trimethylsilyl)amide at about −50° C. to about 25° C.

The process as recited above, for the preparation of the compound of formula:

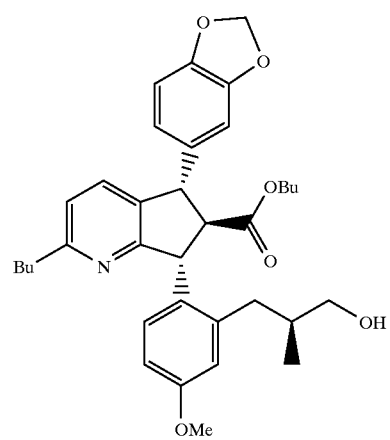

comprising reacting the tertiary alcohol

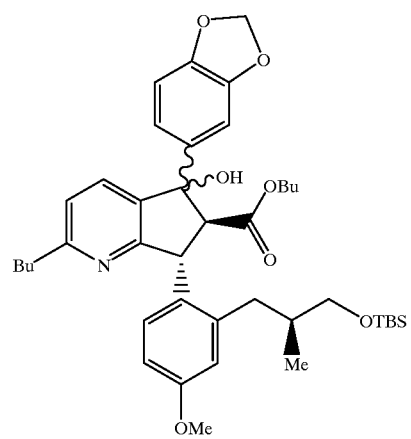

in nitromethane with $Et_3SiH$ and $TiCl_4$ at about −5° C. to about 5° C.

The process as recited above, for the preparation of the compound of formula:

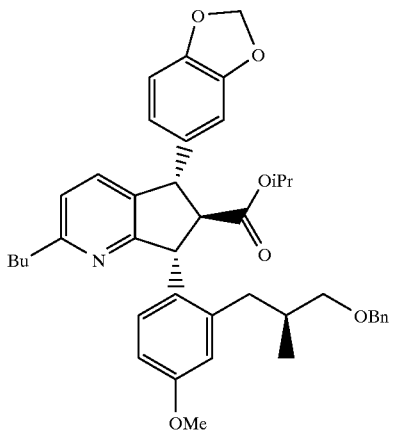

comprising reacting the tertiary alcohol

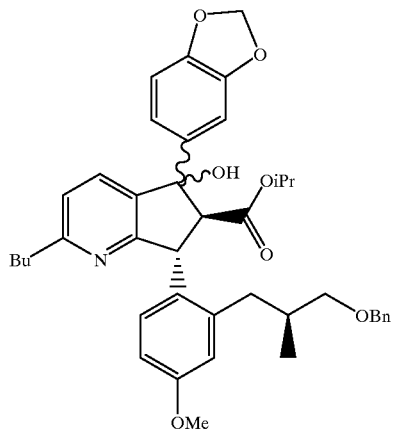

in a solution of isopropyl alcohol and tetrahydrofuran with SmI$_2$ at about 10°–30° C.

The process as recited above, for the preparation of the compound of formula:

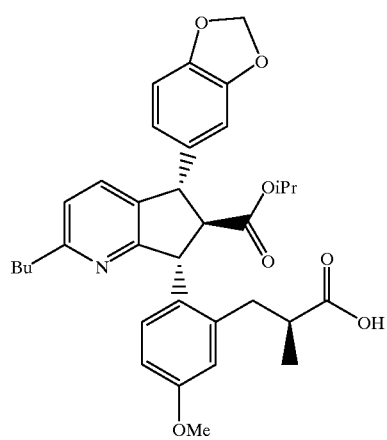

comprising reacting the tertiary alcohol

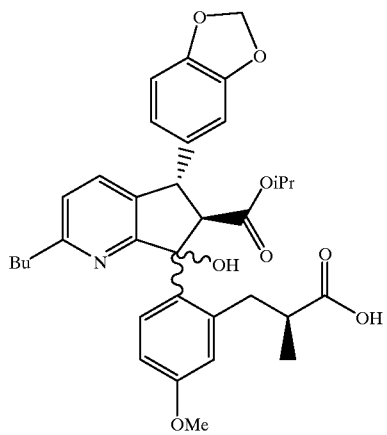

in a solution of isopropyl alcohol and tetrahydrofuran with SmI$_2$ at about 10°–30° C.

It is further understood that the substituents recited above would include the definitions recited below.

The alkyl substituents recited above denote straight and branched chain hydrocarbons of the length specified such as methyl, ethyl, isopropyl, isobutyl, tert-butyl, neopentyl, isopentyl, etc.

The alkenyl-substituents denote alkyl groups as described above which are modified so that each contains a carbon to carbon double bond such as vinyl, allyl and 2-butenyl.

The alkynyl-substituents denote alkyl groups as described above which are modified so that each contains a carbon to carbon triple bond such as ethynyl, and propynyl.

Cycloalkyl denotes rings composed of 3 to 8 methylene groups, each of which may be substituted or unsubstituted with other hydrocarbon substituents, and include for example cyclopropyl, cyclopentyl, cyclohexyl and 4-methylcyclohexyl.

The alkoxy substituent represents an alkyl group as described above attached through an oxygen bridge.

Additionally, it is understood that the terms alkyl, alkenyl, akynyl, cycloalkyl and alkoxy can be substituted with one, two or three substituents selected from the group consisting of: OH, CO$_2$R$^4$, Br, Cl, F, I, CF$_3$, N(R$^5$)$_2$, C$_1$–C$_8$ alkoxy, C$_3$–C$_8$ cycloalkyl, CO(CH$_2$)$_n$CH$_3$, and CO(CH$_2$)$_n$CH$_2$N(R$^5$)$_2$.

The heteroaryl substituent represents an carbazolyl, furanyl, thienyl, pyrrolyl, isothiazolyl, imidazolyl, isoxazolyl, thiazolyl, oxazolyl, pyrazolyl, pyrazinyl, pyridyl, pyrimidyl, purinyl.

The heterocyclyl substituent represents a pyridyl, pyrimidyl, thienyl, furanyl, oxazolidinyl, oxazolyl, thiazolyl, isothiazolyl, pyrazolyl, triazolyl, imidazolyl, imidazoldinyl, thiazolidilnyl, isoxazolyl, oxadiazolyl, thiadiazolyl, morpholinyl, piperidinyl, piperazinyl, pyrrolyl, or pyrrolidinyl.

The α,β-unsaturated ester or amide

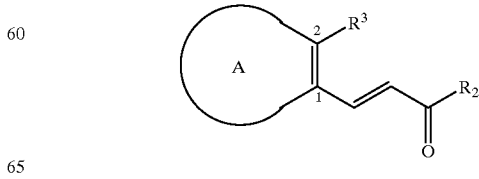

can generally be prepared in two steps:

1) a coupling reaction at the one position of Ring A

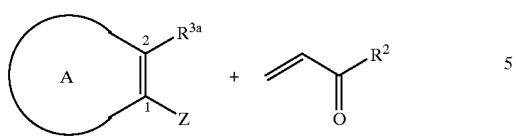

wherein Z is a leaving such as Br, Cl, I, OTriflyl, OTosyl or OMesyl and $R^2$ is $OR^4$ or $N(R^5)_2$; and 2) the conversion of the aldehyde ($R^{3a}$=CHO) to the desired chiral auxiliary ($R^3$), wherein $R^3$ represents

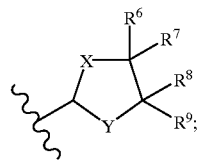

X and Y are independently: O, S, or $NR^5$; $R^4$ is $C_1-C_8$ alkyl; $R^5$ is: H, $C_1-C_8$ alkyl, or aryl; and $R^6$, $R^7$, $R^8$ and $R^9$ are independently: H, $C_1-C_8$ alkyl, and aryl, such that either $R^6$ and $R^7$ are not the same and/or $R^8$ and $R^9$ are not the same, or $R^6$ and $R^8$ or $R^7$ and $R^9$ can join to form a 5- or 6-membered ring, which is unsubstituted or substituted with one, two or three substituents selected from the group consisting of: OH, $CO_2R^4$, Br, Cl, F, I, $CF_3$, $N(R^5)_2$, $C_1-C_8$ alkoxy, $C_1-C_8$ alkyl, $C_2-C_8$ alkenyl, $C_2-C_8$ alkynyl, or $C_3-C_8$ cycloalkyl, $CO(CH_2)_nCH_3$, $CO(CH_2)_nCH_2N(R^5)_2$.

Commercially available pyridone 1 is alkylated via its dianion with propyl bromide, and the product is then converted into the bromopyridine 3a using a brominating agent such as $PBr_3$. The nitrile 3a is then reduced to the aldehyde 3 using diisobutyl aluminum hydride (DIBAL). The aldehyde then undergoes a Heck reaction with t-butyl acrylate using NaOAc, $(allyl)_2PdCl_2$, tri-o-tolylphosphine, toluene, reflux to provide the unsaturated ester 4a in high yield. The unsaturated ester 4a is then reacted with a chiral auxiliary to give the acceptor 5a. Examples of chiral auxiliaries useful in this method are the enantiomers of pseudoephedrine, ephedrine, 1N,2N-dimethyl-diaminocyclohexane, diphenylprolinol, N-methylaminoindanol, and 1N,2N-diethyldiaminocyclohexane.

SCHEME 1

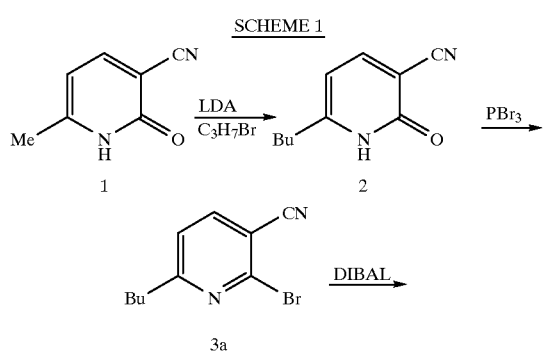

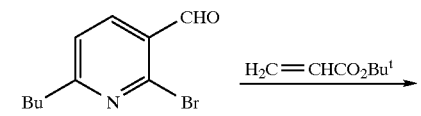

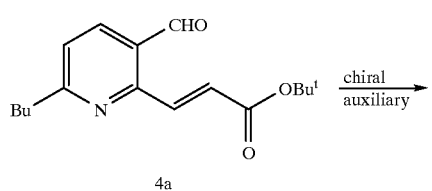

Commericially available acid 10 is reduced with $BH_3.SMe_2$, to the alcohol 11, which is then converted into the bromide 13, via the mesylate 12 using mesyl chloride, triethylamine followed by the addition of NaBr and dimethyl acetamide (DMAC).

SCHEME 2

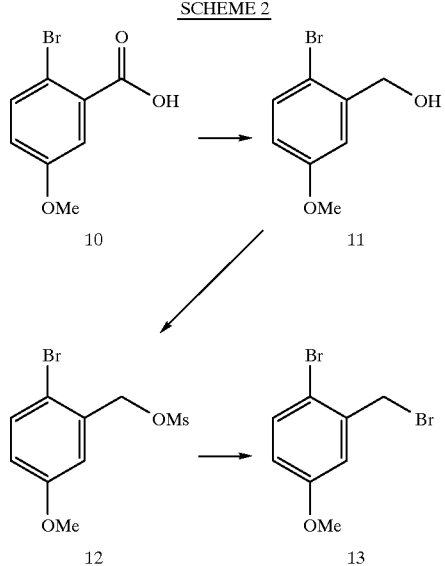

Commercial available 1,2-amino indanol is acylated (propionyl choride, $K_2CO_3$) to give amide 8, which is then converted into the acetonide 9 (2-methoxypropene, pyridinium p-toluene-sulfonate (PPTS)). Acetonide 9 is then alkylated with the bromide 13, (LiHMDS) to give 14, which is then hydrolyzed ($H^+$, MeOH) to give a mixture of acid and methyl ester 15. Reduction (LAH) of the ester/acid mixture provided the alcohol 16 in high yield and optical purity. Protection of the alcohol 16 (TBSCl, imidazole) provided bromide 17, the precursor to organolithium 17a.

SCHEME 3

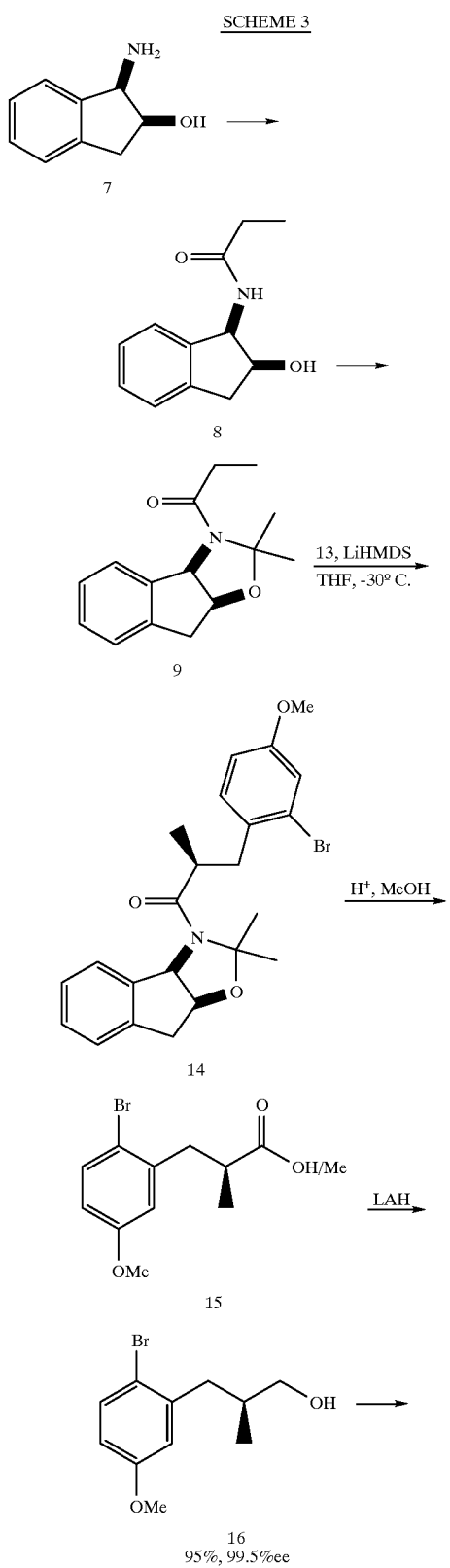

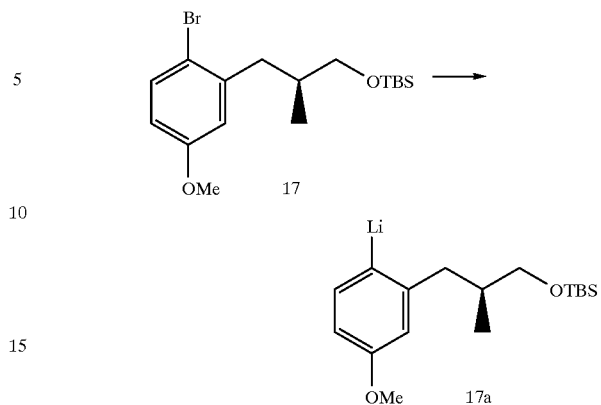

Organolithium reagent 17a was reacted with the acceptor 5a (−78° C. to −50° C.). Workup (acetic acid-THF-water) to remove the chiral auxiliary affords aldehyde 6a in high yield and good selectivity (Scheme 4).

SCHEME 4

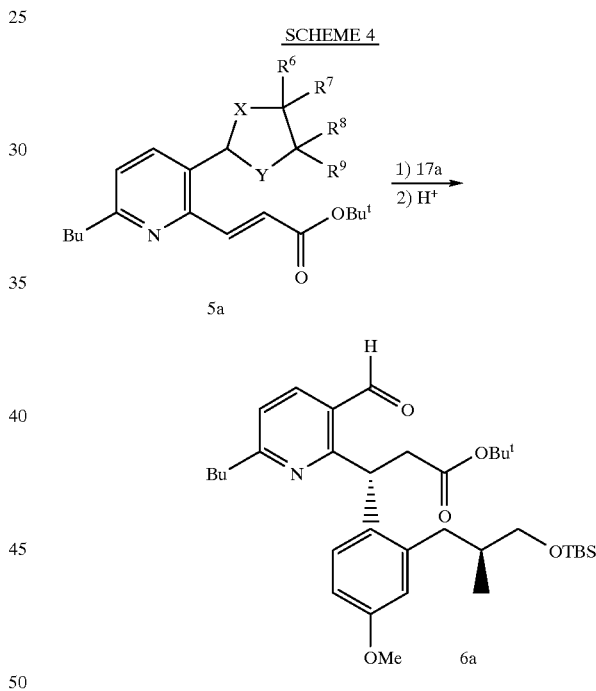

Attempts were made to close the five membered ring via intramolecular alkylation chemistry (Scheme 5). Thus the aldehyde 6a was converted into a 1:1 mixture of chlorides 25 (Grignard addition, then MsCl) which were then reacted with LDA (−78° C.) to give cleanly a 60:40 mixture of 21c and 21a.

SCHEME 5

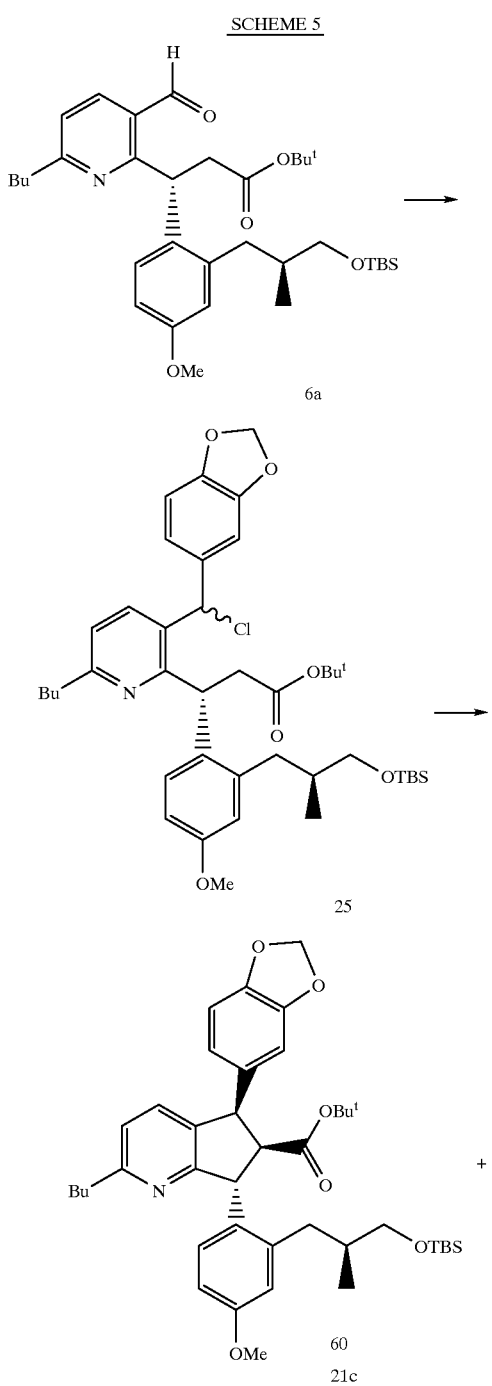

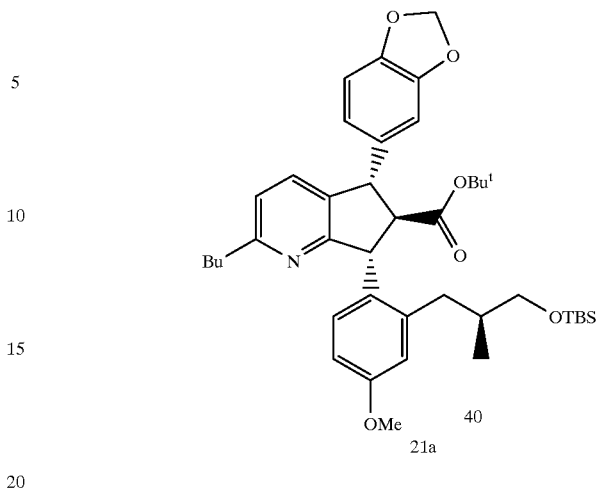

The low stereoselectivity of this alkylation reaction prompted us to develop an alternative ring closure strategy, involving an aldol and stereoselective de-oxygenation sequence (Scheme 6 and Scheme 7). The aldehyde 6a was converted into the keto ester 19 in two steps (85%), involving Grignard addition to give the alcohol 18, followed by oxidation with TPAP. Finally, transesterification of the t-butyl ester (n-BuOH, Ti(OBu)$_4$) provides the n-butyl ester 19 quantitatively (Scheme 6).

SCHEME 6

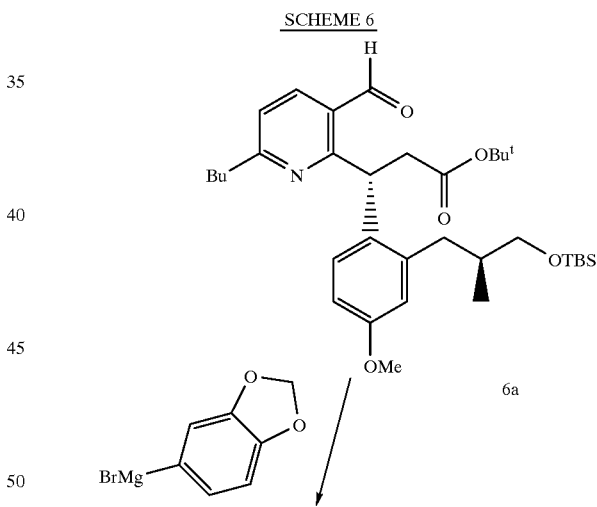

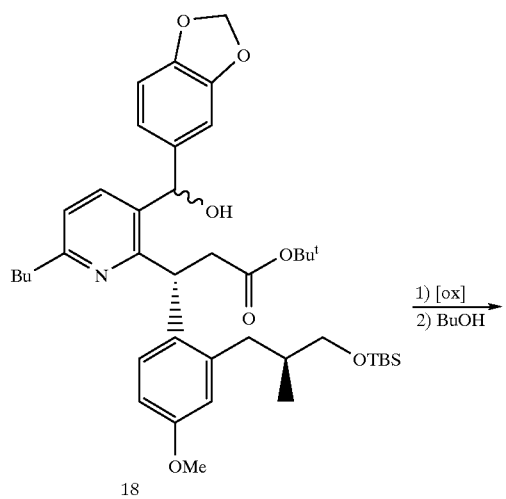

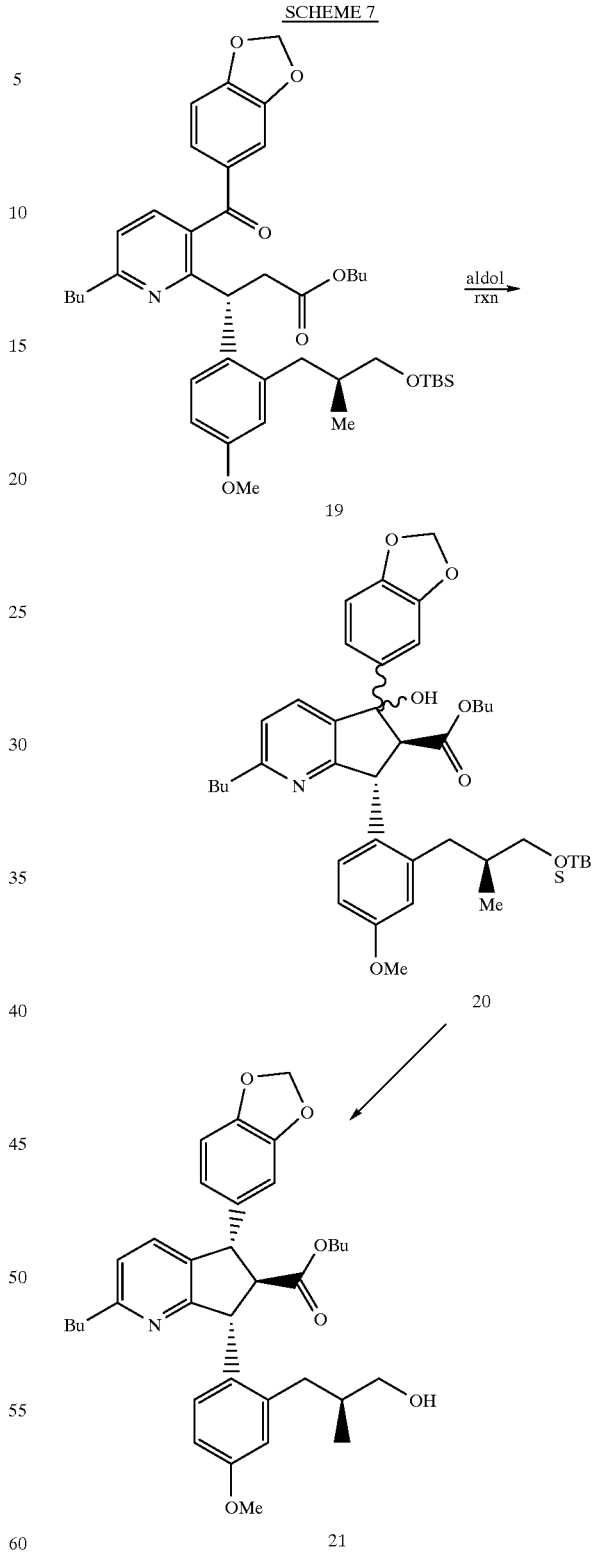

19 undergoes an aldol reaction (LiHMDS, THF, 25° C.) to provide two tertiary alcohols 20 (1:1), which were de-oxygenated cleanly to give the desired heterocycle 21 in excellent yield (75% for three steps). The selectivity in this reaction was estimated by $^1$H NMR to be >90% de (Scheme 7). The de-oxygenation step can be carried out using a reducing agent including but not limited to trialkylsilyl hydride or samarian iodide, using an acid with the hydride reducing agent. This aldol reaction and de-oxygenation sequence can be carried out with a variety of ketones, such as —COaryl and —COheteraryl.

Oxidation of the side chain hydroxyl 21 to the carboxylic acid 22 was effected using standard conditions (cat RuCl$_3$-NaIO$_4$, CH$_3$CN, or two steps involving i) Sulfur trioxide pyridine complex-dimethyl sulfoxide, ii) sodium chlorite-tert butanol). Subsequent hydrolysis (NaOH-MeOH) of 22 provided the target compound 23 cleanly. The $^1$H and $^{13}$C NMR spectrum of this material was identical with that of the authentic target compound (Scheme 8).

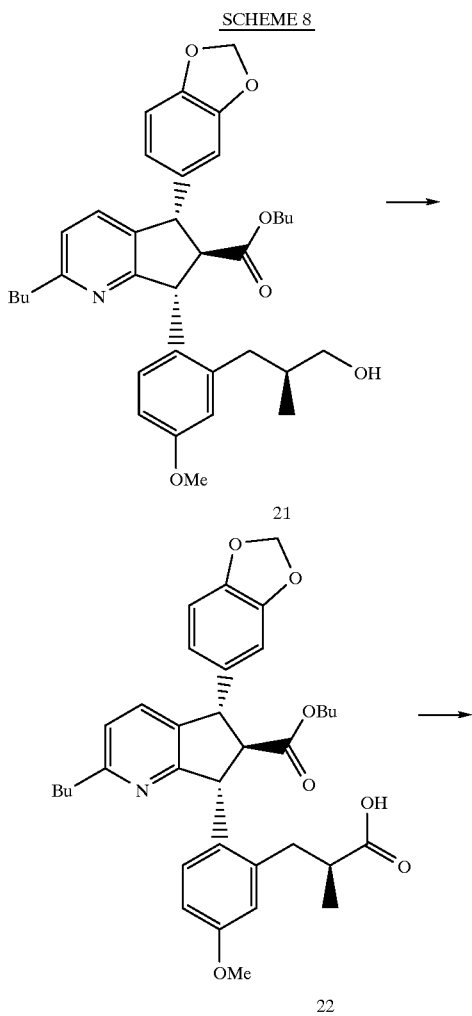

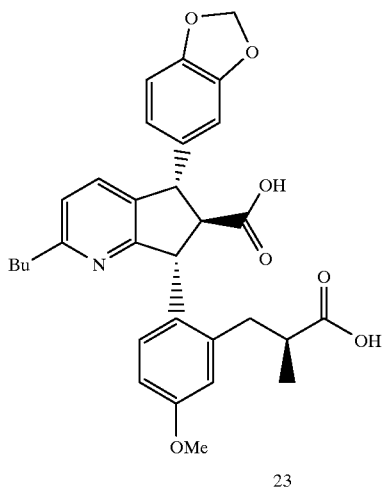

Scheme 9 describes the preparation of the isopropyl ester analog of compound 23 described in Scheme 8. Unsaturated oxazoline 25 was prepared via the Horner-Emmons reaction of phosphonate 24 with the bromopyridine aldehyde 3. Conjugate addition of the lithium anion of 4-bromo-1,2-(methylenedioxy)benzene to 25 produced the desired adduct 26 with in high diastereomeric excess.

Hydrolysis of oxazoline 26 was accomplished by refluxing in isopropyl alcohol with concentrated sulfuric acid to yield the isopropyl ester (not shown in scheme).

Subsequent carbonylation of the isopropyl ester using catalytic palladium in methanol produced diester 27. Inverse addition of the lithium anion of 17 to methyl ester 27 at –78° C. generated the desired ketoester 28. Compound 28 was then treated with aqueous HF to remove the silyl protecting group. The deprotected alcohol was then cyclized with sodium t-amylate to form the aldol adduct 29. Finally, aldol adduct 29 was oxidized to the carboxylic acid, and then stereoselectively deoxygenated by the action of SmI$_2$ to produce 30 as a single diastereomer.

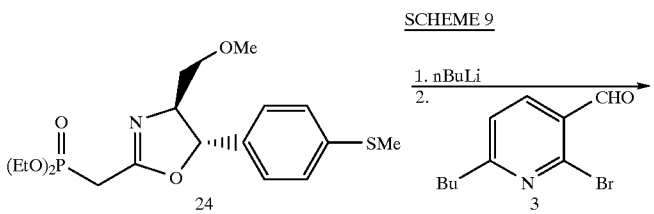

SCHEME 9

-continued
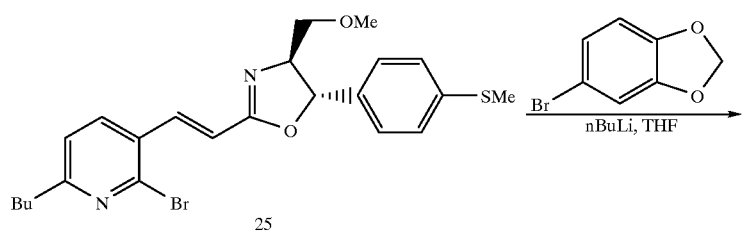
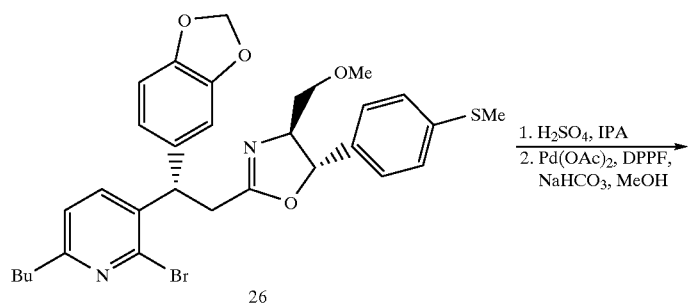
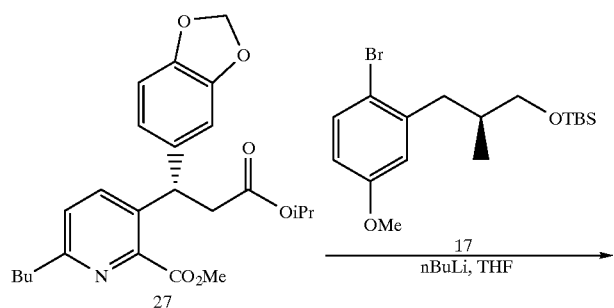
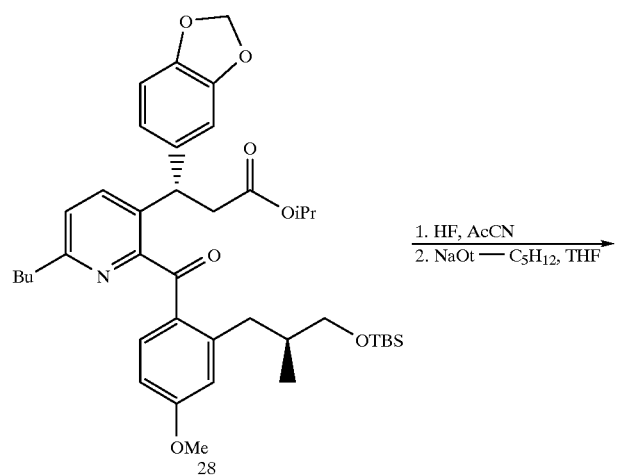

-continued

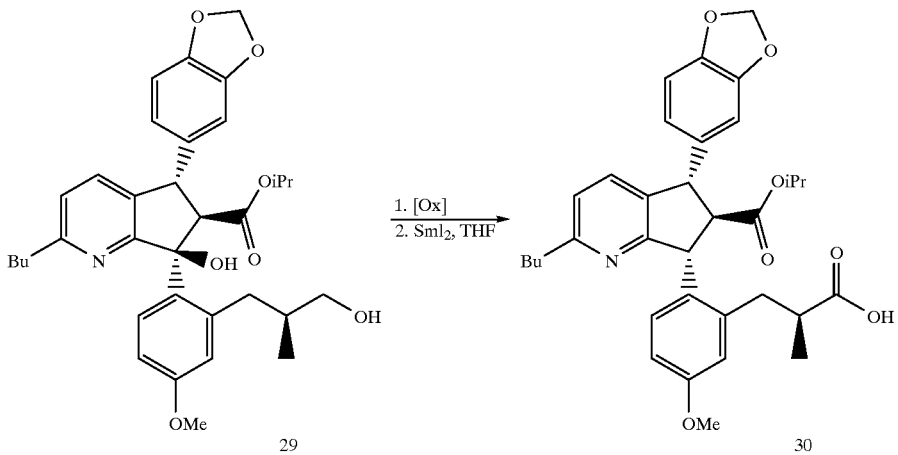

The instant invention can be understood further by the following examples, which do not constitute a limitation of the invention. Note that the reference numbers utilized in the examples below do not necessarily correspond with the reference numbers utilized in the Schemes.

EXAMPLE 1

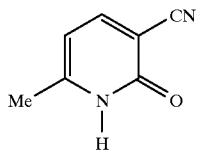

Preparation of 1

Compound 1 is a commercially available starting material, for example, see Aldrich Chemical Company, Milwaukee, Wis., USA 53201.

EXAMPLE 2

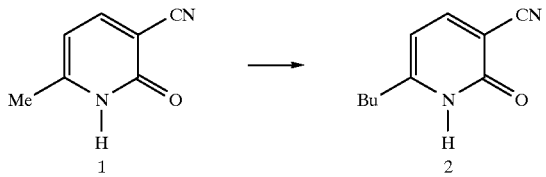

Preparation of 2

Diisopropyl amine (MW 101.19, d 0.772, 2.1 equ, 20.54 mL) in 200 mL THF. Cool to −50° C. and add n-BuLi (1.6M in hexanes, 2.05 equ, 96 mL), allowing solution to warm to −20° C. Age 0–3° C. for 15 min, then cool to −30° C. and add 1 (MW 134.14, 75 mmol, 10.0 g). Age 0° C. to 43° C. for 2 h. Cool to −50° C. and add bromopropane (MW 123.00, d 1.354, 1.0 equ, 6.8 mL). Warm to 25° C. over 30 min, and age 30 min. Add NH$_4$Cl and CH$_2$Cl$_2$. Dry organic (magnesium sulfate) then evaporate in vacuo to afford 61% of 2.

EXAMPLE 3

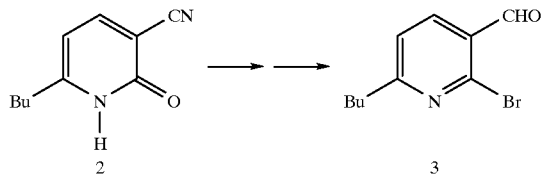

Preparation of 3

Mix 2 (MW 176.22, 46 mmol) and PBr$_3$ (MW 270.70, d 2.880, 2.5 equ, 10.8 mL) and age at 160° C. After 2 h, cool to 25° C. and add some CH$_2$Cl$_2$. Slowly quench by adding water. Separate layers and wash aqueous two times with CH$_2$Cl$_2$. Combine organic layers and dry (magnesium sulfate). Concentrate and isolate solid by silica gel chromatography (90:10 hexanes:ethyl acetate) in 60% yield (MW 239.12, 6.60 g).

Dissolve product of bromination reaction (MW 239.12, 27.6 mmol, 6.60 g) in 66 mL toluene and cool to −42° C. Slowly add DIBAL (1.5M in toluene, 2 equ, 37 mL) and age 1 h at −42° C. Add HCl (2N, 10 equ, 134 mL) and stir vigorously for 30 min. Dilute with ethyl acetate, separate layers, and wash aqueous with ethyl acetate. Combine organic layers, dry (magnesium sulfate), and concentrate in vacuo to afford 90% (MW 242.11, 6.01 g) of 3.

EXAMPLE 4a

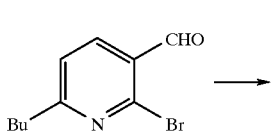

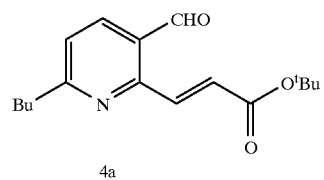

Preparation of 4a

Dissolve 3 (MW 242.11, 24.8 mmol, 6.01 g) in 75 mL toluene. Add sodium acetate (MW 82, 3 equ, 6.13 g), t-butyl acrylate (MW 128.17, d 0.875, 2.5 equ, 9.08 mL), P(o-tolyl)$_3$ (MW 304.38, 10 mol %, 755 mg) and allyl palladium chloride dimer (MW 365.85, 5 mol %, 455 mg). Age at reflux for 24 h. Cool, filter and evaporate in vacuo. Isolate 4a (MW 289.37) by silica gel chromatography (92:8 hexanes:ethyl acetate) in 80% yield (5.74 g).

EXAMPLE 4b

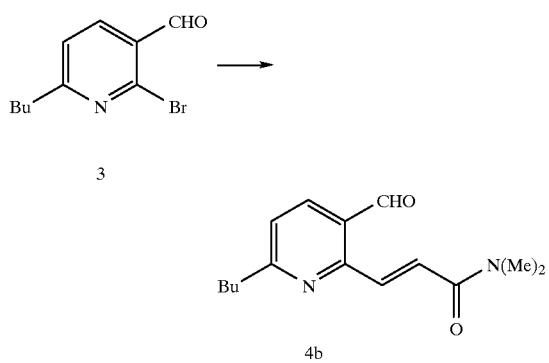

Preparation of 4b

Dissolve 3 (MW 242.11, 24.8 mmol, 6.01 g) in 75 mL toluene. Add sodium acetate (MW 82, 3 equ, 6.13 g), dimethylacrylamide (MW 99.13, d 0.962, 1 equ, 2.55 mL), PPh$_3$ (MW 262.29, 10 mol %, 653 mg) and allyl palladium chloride dimer (MW 365.85, 5 mol %, 455 mg). Age at 140° C. in sealed tube for 24 h. Cool, filter and evaporate in vacuo. Isolate 4b (MW 260.34) by silica gel chromatography (80:20 hexanes:ethyl acetate) in 70% yield (4.52 g).

EXAMPLE 5a

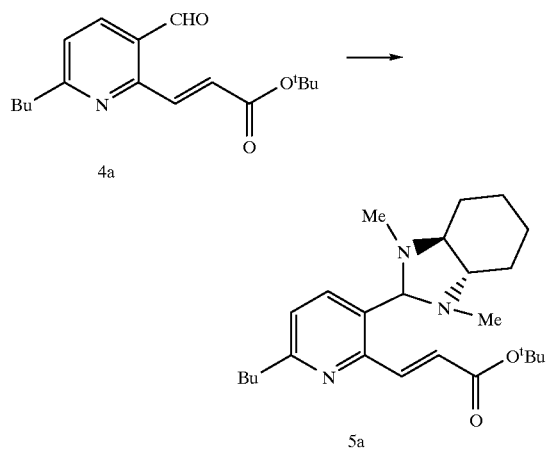

Preparation of 5a

Dissolve 4a (MW 289.37, 19.8 mmol, 5.74 g) in 53 mL CH$_2$Cl$_2$. Add (1R,2R)-N,N-dimethylcyclohexanediamine (MW 142.24, 1 equ, 2.83 g) and sieves (powdered, 1 wt equ, 5.74 g) and age 25° C. for 8 h. Filter and concentrate filtrate in vacuo to afford 5a (MW 413.60, 8.19 g) in quantitative yield.

EXAMPLE 5b

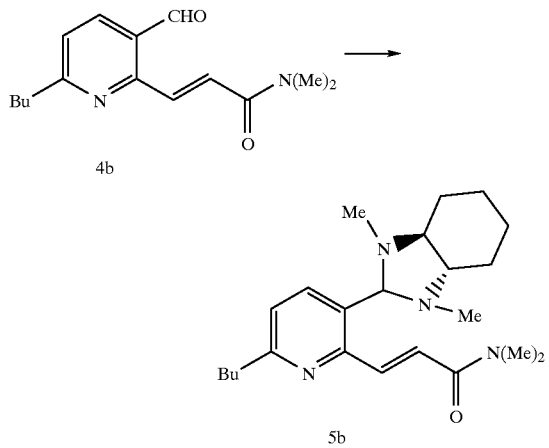

Preparation of 5b

Dissolve 4b (MW 260.34, 17.4 mmol, 4.53 g) in 40 mL CH$_2$Cl$_2$. Add (1R,2R)-N,N-dimethylcyclohexanediamine (MW 142.24, 1 equ, 2.47 g) and sieves (powdered, 1 wt equ, 4.53 g) and age 25° C. for 8 h. Filter and concentrate filtrate in vacuo to afford 5b (MW 384.57, 6.69 g) in quantitative yield.

EXAMPLE 5c

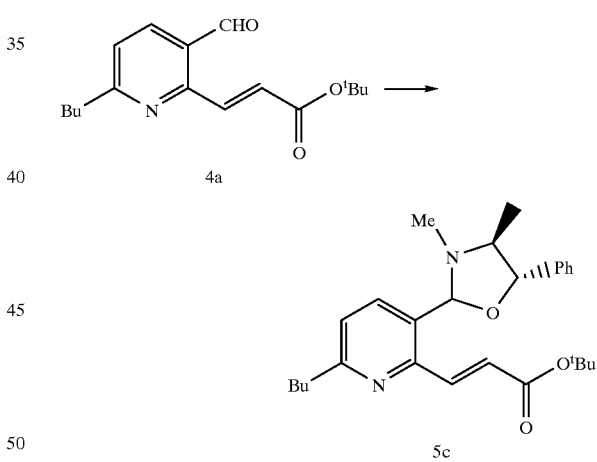

Preparation of 5c

Dissolve 4a (MW 289.37, 19.8 mmol, 5.74 g) in 53 mL toluene. Add (S,S)-pseudoephedrine (MW 165.24, 1.1 equ, 3.60 g) and 4 drops of concentrated HCl. Reflux with a Dean-Stark trap for 2h. Wash with saturated aqueous NaHCO$_3$ and extract with ethyl acetate. Dry organic layer with MgSO$_4$, then filter and concentrate filtrate in vacuo to afford 5c (MW 4436.59, 8.64 g) in quantitative yield. $^1$H NMR (CDCl$_3$): 8.23 (d, J=11.78, 1 H), 7.88 (d, J=7.33, 1 H), 7.39 (m, 5 H), 7.16 (d, J=7.33, 1 H), 7.02 (d, J=11.78, 1 H), 5.31 (s, 1 H), 4.80 (d, J=9.18, 1 H), 2.80 (t, J=5.79, 2 H), 2.59 (m, 1 H), 2.19 (s, 3 H), 1.72 (m, 2 H), 1.56 (s, 9 H), 1.39 (m, 2 H), 1.27 (d, J=4.83, 3 H), 0.94 (t, J=6.76, 3 H).

EXAMPLE 5d

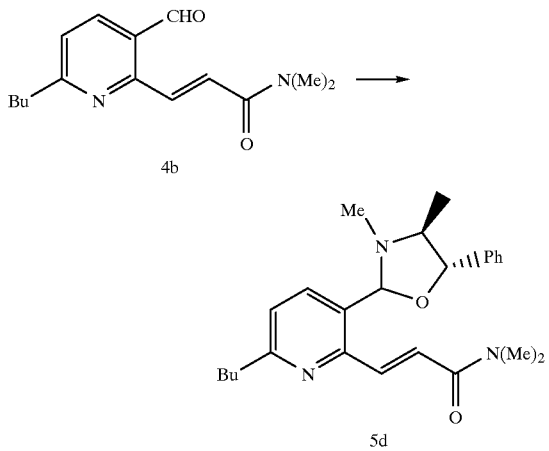

Preparation of 5d

Dissolve 4b (MW 260.34, 117.4 mmol, 5.74 g) in 53 mL toluene. Add (S,S)-pseudoephedrine (MW 165.24, 1.1 equ, 3.16 g) and 4 drops of concentrated HCl. Reflux with a Dean-Stark trap for 2h. Wash with saturated aqueous NaHCO$_3$ and extract with ethyl acetate. Dry organic layer with MgSO$_4$, then filter and concentrate filtrate in vacuo to afford 5c.

EXAMPLE 6a

Preparation of 6a

Dissolve 17 (see Example 17, MW 373.41, 2 equ, 14.79 g) in 85 mL THF. Cool to −78° C. and add t-BuLi (1.7 M in pentane, 4 equ, 46.6 mL), maintaining temperature below −70° C. Age 15 min, then slowly add solution of 5c (MW 436.59, 19.8 mmol, 8.64 g) in 65 mL THF. Age 1 h at −78° C., then cannula into cold aq NH$_4$Cl (100 mL). Add ethyl acetate and separate layers. Wash aqueous with ethyl acetate. Combine organic layers and wash with brine, then dry (magnesium sulfate) and evaporate in vacuo. $^1$H NMR provides de data. Add THF (75 mL), acetic acid (AcOH) (30 mL) and water (10 mL). Age 5 h at 25° C. Separate layers and wash aqueous two times with ethyl acetate. Combine organic layers, wash with brine, dry (magnesium sulfate), and evaporate in vacuo. 6a (MW 583.89) is isolated in 85% yield (9.83 g) by silica gel chromatography (92:8 hexanes-:ethyl acetate). $^1$H NMR (C$_6$D$_6$): 10.5 (s, 1 H), 7.72 (d, J=7.85, 1 H), 7.30 (d, J=8.64, 1 H), 6.83 (d, J=8.05, 1 H), 6.59 (dd, J=8.65, 2.61, 1 H), 6.56 (d, J=7.99, 1 H), 5.92 (m, 1 H), 3.85 (dd, J=16.32, 10.77, 1 H), 3.48 (m, 2 H), 3.32 (s, 3 H), 3.01 (dd, J=14.11, 6.77, 1 H), 2.87 (dd, J=16.30, 3.91, 1 H), 2.79 (dd, J=13.25, 6.21, 1 H), 2.68 (t, J=7.66, 2 H), 2.10 (m, 1 H), 1.72 (m, 2 H), 1.30 (s, 9 H), 1.25 (m, 2 H), 1.01 (s, 9 H), 0.95 (d, J=6.42, 3 H), 0.94 (t, J=8.40, 3 H), 0.10 (d, J=5.83, 6 H).

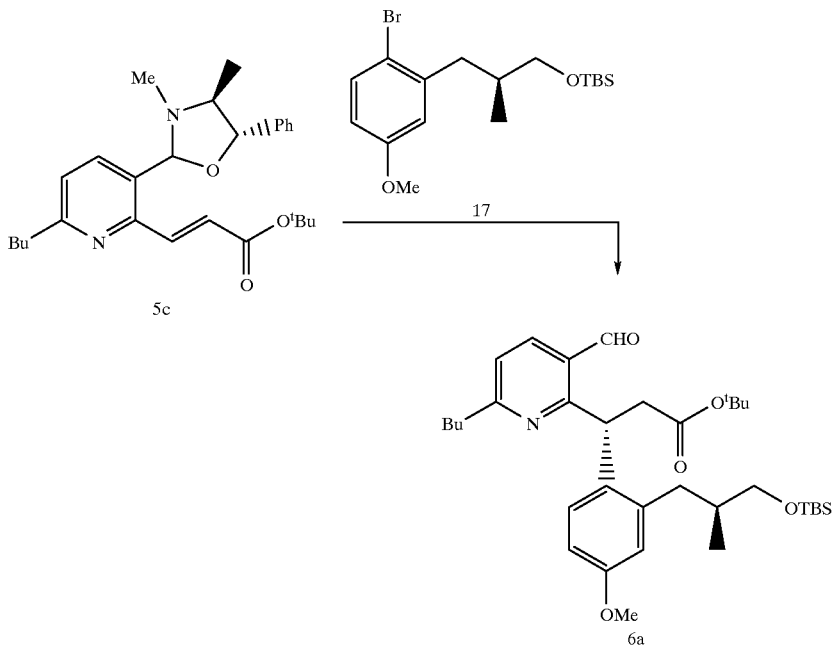

EXAMPLE 6b

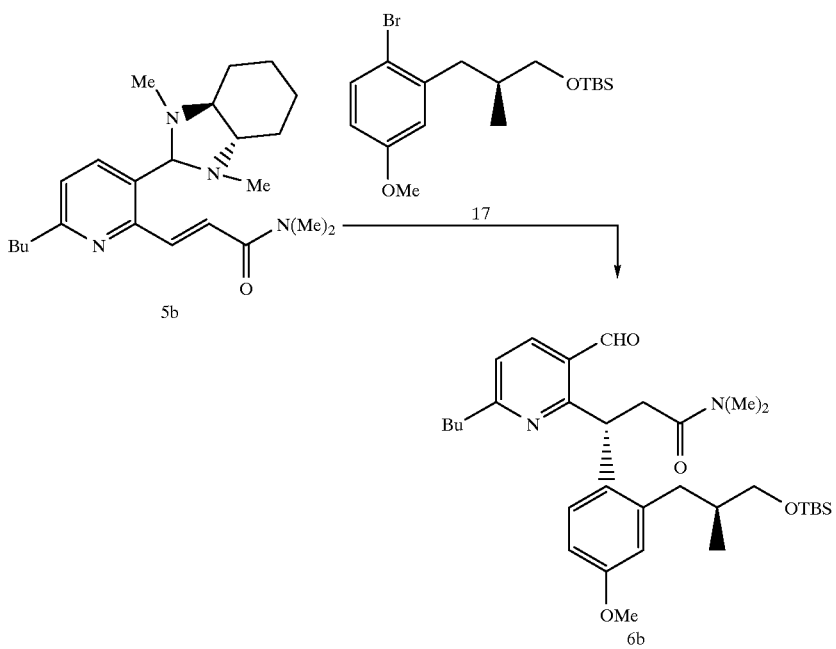

Preparation of 6b

Dissolve 17 (see Example 17, MW 373.41, 2 equ, 12.99 g) in 70 mL THF. Cool to −78° C. and add t-BuLi (1.7 M in pentane, 4 equ, 40.9 mL), maintaining temperature below −70° C. Age 15 min, then slowly add solution of 5b (MW 384.57, 17.4 mmol, 6.69 g) in 55 mL THF. Age 1 h at −78° C., then cannula into cold aq NH$_4$Cl (100 mL). Add ethyl acetate and separate layers. Wash aqueous with ethyl acetate. Combine organic layers and wash with brine, then dry (magnesium sulfate) and evaporate in vacuo. $^1$H NMR provides de data. Add THF (55 mL), AcOH (20 mL) and water (8 mL). Age 5 h at 25° C. Separate layers and wash aqueous two times with ethyl acetate. Combine organic layers, wash with brine, dry (magnesium sulfate), and evaporate in vacuo. 6b (MW 678.99) is isolated in 75% yield (8.86 g) by silica gel chromatography (70:30 hexanes:ethyl acetate). $^1$H NMR (CDCl$_3$): 10.30 (s, 1 H), 7.99 (d, J=4.74, 1 H), 7.11 (d, J=3.19, 1 H), 6.89 (d, J=8.61, 1 H), 6.78 (d, J=2.76, 1 H), 6.59 (t, J=2.78, 1 H), 5.70 (t, J=2.86, 1 H), 3.87 (dd, J=11.18, 4.29, 1 H), 3.74 (s, 3 H), 3.58 (m, 2 H), 3.11 (s, 3 H), 3.25 (dd, J=14.35, 6.25, 1 H), 2.88 (s, 3 H), 2.84 (m, 2H), 2.68 (dd, J=14.35, 8.30, 1 H), 2.47 (dd, J=9.02, 2.89, 1 H), 2.09 (m, 1 H), 1.75 (m, 2 H), 1.39 (m, 2 H), 0.99 (t, J=3.49, 3 H), 0.92 (s, 9 H), 0.92 (d, J=7.15, 6 H), 0.08 (d, J=1.91, 6 H).

$^{13}$C NMR (CDCl$_3$): 190.5, 171.6, 165.9, 163.7, 157.9, 139.3, 137.2, 135.5, 130.0, 127.1, 120.8, 115.5, 111.7, 67.8, 55.11, 39.7, 38.9, 38.4, 37.2, 36.8, 36.0, 35.4, 26.0 (3 C), 22.3, 18.4, 17.3, 14.7, −5.3 (2 C).

EXAMPLE 7

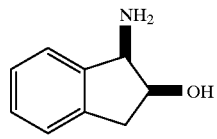

Preparation of 7

Compound 7 is a commercially available starting material, for example, see DSM Andeno, Grubbenvorsterweg 8, P.O. Box 81, 5900 AB Venlo, The Netherlands.

EXAMPLE 8

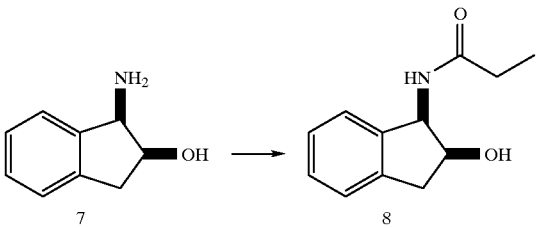

Preparation of 8

Na$_2$CO$_3$ (MW 105.99, 1.5 equ, 8.8 g) dissolved in 82 mL water. Add a solution of (1R,2S) aminoindanol 7 (MW 149.19, 55.0 mmol, 8.2 g) in 160 mL CH$_2$C$_2$. Cool to −5° C. and add propionyl chloride (MW 92.53, d 1.065, 1.3 equ, 6.2 mL). Warm to 25° C. and age 1 h. Separate layers and dry organic (magnesium sulfate). Concentrate in vacuo to afford 8 (MW 205.26, 10 g) in 89% isolated yield.

EXAMPLE 9

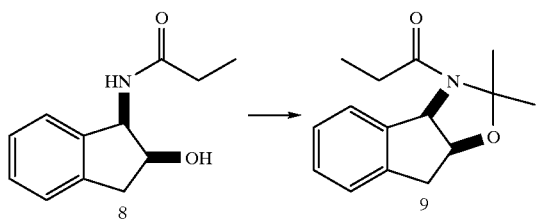

Preparation of 9

To a solution of 8 (MW 205.26, 49.3 mmol, 10 g) in 200 mL THF, add pyridinium p-toluenesulfonate (PPTS) (MW 251.31, 0.16 equ, 2g) then methoxypropene (MW 72.11, d 0.753, 2.2 equ, 10.4 mL). Age 2 h at 38° C., then add aqueous sodium bicarbonate and ethyl acetate. The organic layer was dried (magnesium sulfate). After concentration in vacuo, 9 (MW 245.32, 12.09 g) was formed in quantitative yield.

EXAMPLE 10

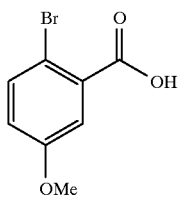

Preparation of 10

Compound 10 is a commercially available starting material, for example, see Lancaster Synthesis, P.O. Box 1000, Windham, N.H. 03087-9977 or Ryan Scientific, Inc., P.O. Box 845, Isle of Palms, S.C. 29451-0845.

EXAMPLE 11

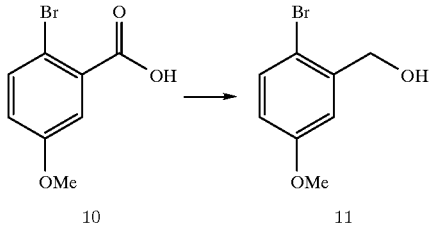

Preparation of 11

10 (MW 231.05, 130 mmol, 30.0 g) in 300 mL $CH_2Cl_2$ at 0° C. Add $BH_3$-$SMe_2$ (3 equ, 25.2 mL) and age for 2 h at 25° C. Quench into aqueous 2 N HCl and separate layers. Dry organic (magnesium sulfate) and concentrate in vacuo to obtain 94% yield of 11 (MW 217.06, 25.5 g).

EXAMPLE 12

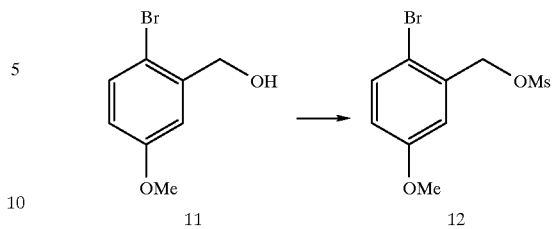

Preparation of 12

Dissolve 11 (MW 217.06, 47.2 mmol, 10.24 g) in 55 mL $CH_2Cl_2$ and cool to −20° C. Add DIEA (MW 129.25, d 0.742, 1.3 equ, 10.69 mL) then methane sulfonyl chloride (MsCl) (MW 114.55, d 1.480, 1.2 equ, 4.38 mL). Age −5° C. to 0° C. for 1 h then quench into 55 mL water. Extract with $CH_2Cl_2$ then wash with 1N $H_2SO_4$ (40 mL), then brine. Dry organic layers (magnesium sulfate) and concentrate in vacuo to afford 12 (MW 295.15, 13.23 g) in 95% yield.

EXAMPLE 13

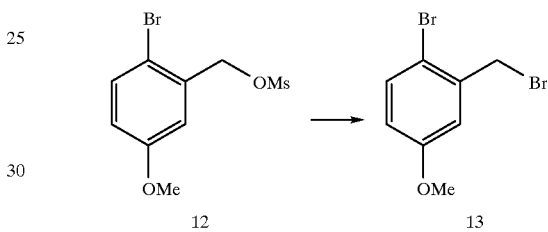

Preparation of 13

12 (MW 295.15, 44.8 mmol, 13.23 g) in 44 mL dimethylacetamide (DMAC). Add NaBr (MW 102.90, 2 equ, 9.22 g) and age 1h. Add 88 mL water and collect solid by filtration. Wash cake with water and dry by suction. Quantitative yield of 13 (MW 279.96, 12.54 g) is obtained.

EXAMPLE 14

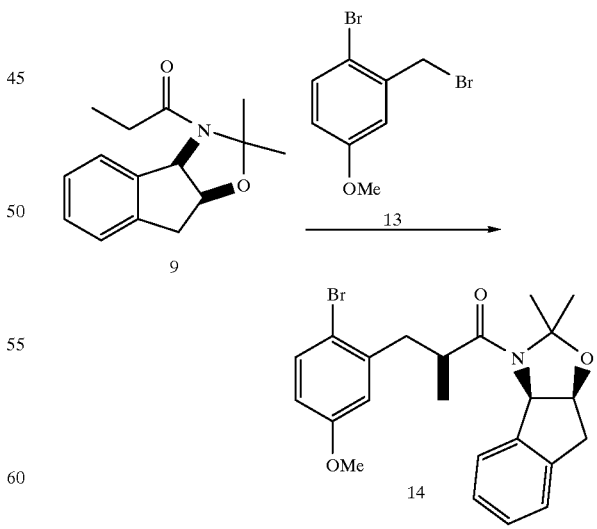

Preparation of 14

9 (MW 245.32, 1.1 equ, 89.1 g) in 1 L THF, cooled to −50° C. Add lithium bis(trimethylsilyl)amide (LiHMDS) (1.0 M in THF, 1.5 equ, 545 mL) and age 1.5 h, warming to −30° C. Add 13 (MW 279.96, 327 mmol, 91.3 g) in 300 mL THF, and age −35° C. for 1 h. Warm to −10° C. over 1 h, then quench into aqueous NH₄Cl. Separate layers and extract with ethyl acetate. Dry organic and concentrate in vacuo to afford crude 14 (MW 444.37).

EXAMPLE 15

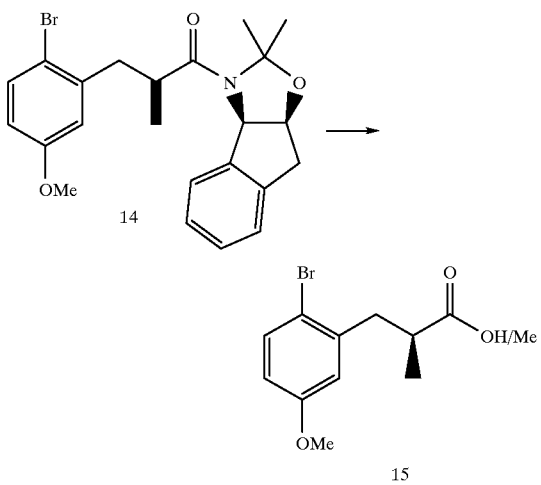

Preparation of 15

14 in 1 L MeOH and cooled to 10° C. Bubble in HCl gas for 1 h until reaction is complete. 2 L H₂O added and the product was filtered. The cake was washed with H₂O and dried to give the product hydroxyamide, which was then dissolved in 1 L MeOH and 1.5 L 6N HCl and refluxed overnight. The mixture was cooled to 25° C. and extracted with CH₂Cl₂ to give, after concentration, compounds 15 (60 g, 64% from bromide 13).

EXAMPLE 16

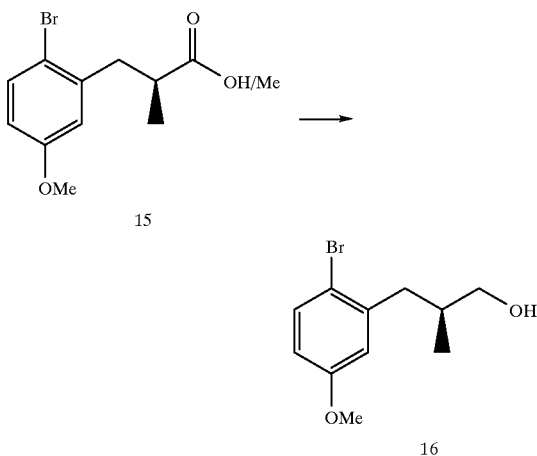

Preparation of 16

15 (mixture of acid and ester, 26.88 mmol) in 150 mL THF at −78° C. Add lithium aluminum hydride (LiAlH₄) (1 M in THF, 2 equ, 53.76 mL) over 30 min. Warm to 25° C. over 1 h, then quench into aqueous NH₄Cl. Add ethyl acetate, extract ethyl acetate. Wash organics with brine, dry (magnesium sulfate), and concentrate in vacuo to afford 95% yield of 16 (MW 259.14, 6.62 g).

EXAMPLE 17

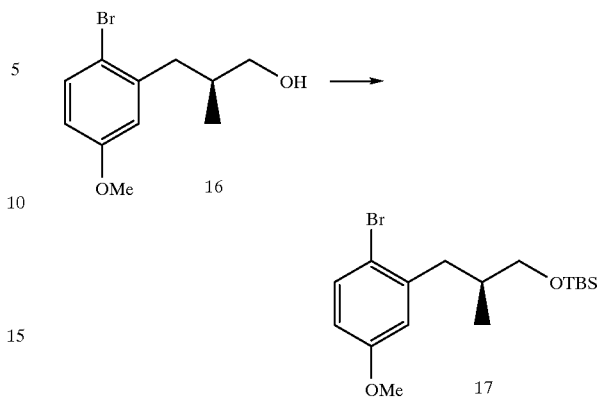

Preparation of 17

16 (MW 259.14, 25.54 mmol, 6.62 g) in 35 mL CH₂Cl₂ and cool to 0° C. Add imidazole (MW 68.08, 2.5 equ, 4.35 g) and then tert-butyldimethylsilyl chloride (TBSCl) (MW 150.73, 1 equ, 3.85 g). Age 1 h at 25° C. then quench with aqueous NaHCO₃ and add ethyl acetate. Extract with ethyl acetate, then dry organic layer (magnesium sulfate) and concentrate in vacuo to afford a quantitative yield of 17 (MW 373.41, 9.54 g). $^1$H NMR (CDCl₃): 7.41 (d, J=8.74, 1H), 6.77 (d, J=3.04, 1H), 6.63 (dd, J=8.73, 3.06, 1H), 3.78 (s, 3 H), 3.50 (d, J=5.75, 2 H), 2.89 (dd, J=13.31, 6.15, 1 H), 2.45 (dd, J=13.30, 8.26, 1 H), 2.03 (m, 1 H), 0.94 (s, 9 H), 0.92 (d, J=5.01, 3 H), 0.07 (s, 6 H).

$^{13}$C NMR (CDCl₃): 159.1, 141.6, 133.2, 117.0, 115.4, 113.2, 67.4, 55.4, 39.7, 36.3, 26.0 (3C), 18.4, 16.5, −5.3 (2C).

EXAMPLE 18

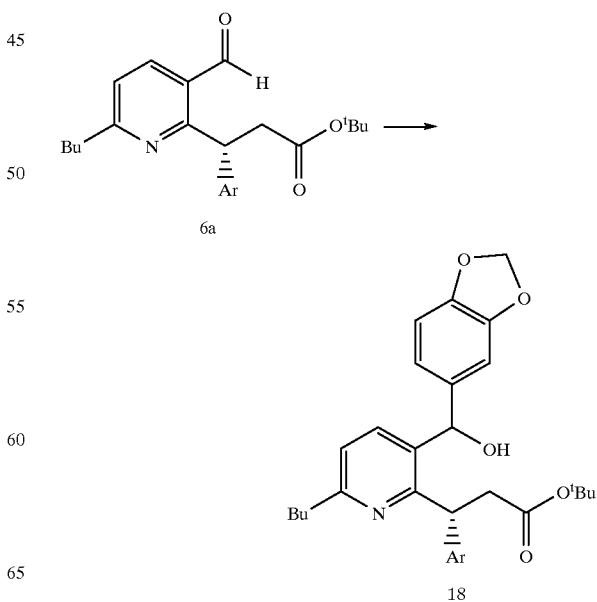

-continued

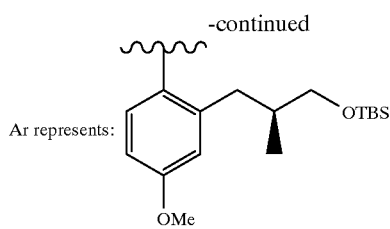

Ar represents:

Preparation of 18

Prepare 0.5 M Grignard solution from 4-bromo-1,2-(methylenedioxy)benzene (MW 201.01, 42.1 mmol, 8.46 g) and Mg (MW 24.31, 1.5 equ, 1.54 g) in 84 mL THF. Dissolve 6a (MW 583.89, 16.8 mmol, 9.83 g) in 80 mL THF and cool to −78° C. Slowly add Grignard solution (2.5 equ, 0.5 M, 84 mL) and age 30 min. Quench into aqueous NH₄Cl and add ethyl acetate. Wash organic with brine, dry (magnesium sulfate) and evaporate in vacuo. Carry crude into oxidation.

EXAMPLE 19

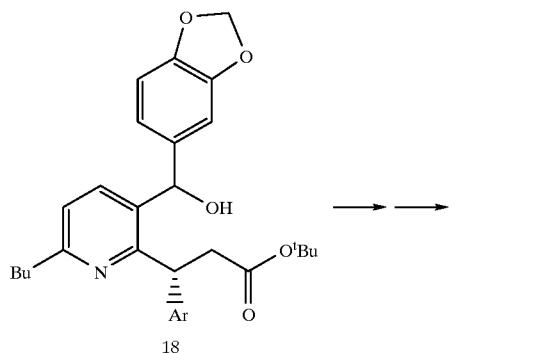

Preparation of 19

Crude 18 (MW 706.01, 16.8 mmol) in 150 mL ACN. Add NMO (MW 117.15, 3 equ, 5.90 g), sieves (powdered, 3 wt equ, 35.6 g), and TPAP (MW 351.43, 10 mol %, 590 mg) and age 25° C. for 2 h. Concentrate to remove ACN, then elute through silica gel pad with ethyl acetate. Concentrate in vacuo, then chromatograph (90:10 hexanes:ethyl acetate) to isolate the oxidation product (85% yield over two steps).

Dissolve in 100 mL n-BuOH and add Ti(OBu)4 (MW 340.366, 5 equ, 28.59 g). Reflux for 48 h, then quench into water and add ethyl acetate. Filter through celite, separate the layers, and wash the organic with brine. Dry (magnesium sulfate) and evaporate in vacuo to afford 81% yield (over three steps) of 19 (MW 703.99, 9.58 g).

EXAMPLE 20

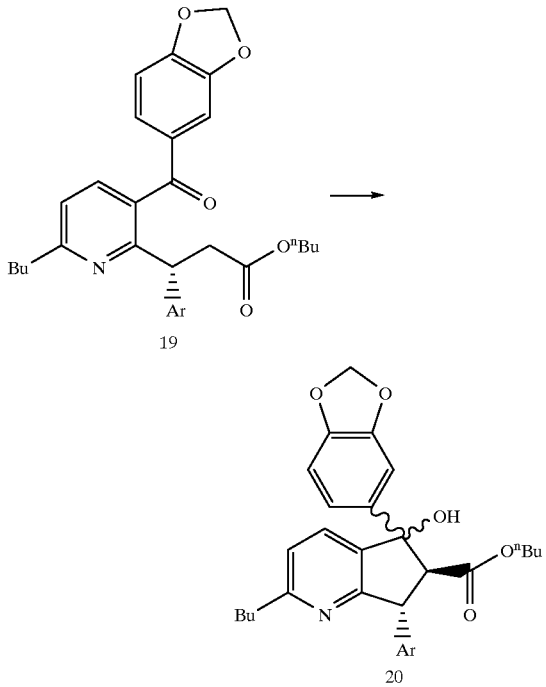

Preparation of 20

Dissolve 19 (MW 703.99, 13.6 mmol, 9.58 g) in 75 mL THF and cool to −50° C. Slowly add LiHMDS (1.0 M in THF, 5 equ, 68.0 mL) and age 25° C. for 16 h. Quench into aqueous NH₄Cl and add ethyl acetate. Wash organic with brine, dry (magnesium sulfate) and evaporate in vacuo to afford 20 (MW 703.99).

EXAMPLE 21

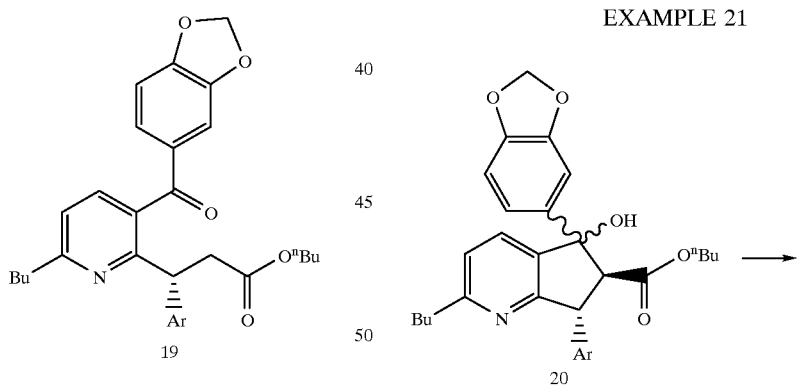

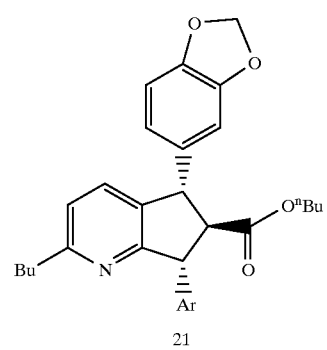

Preparation of 21

Dissolve 20 (MW 703.99, 13.6 mmol) in 125 ml nitromethane and add Et₃SiH (MW 116.28, d 0.728, 10 equ, 21.7 mL). Cool to 0° C. and slowly add TiCl₄ (1.0 M in CH₂Cl₂, 4 equ, 54.4 mL) and age 1 h at 0° C. Quench into 2N HCl and dilute with ethyl acetate. Wash aqueous with ethyl acetate, then combine organics and wash with brine. Dry (magnesium sulfate) and evaporate in vacuo. Isolate by silica gel chromatography (75:25 hexanes:ethyl acetate) to afford a 75% yield (over two steps) of 21 (MW 573.73, 5.85 g). ¹H NMR (CDCl₃): 7.20 (d, J=7.80, 1 H), 6.95 (d, J=7.83, 1 H), 6.88 (d, J=8.37, 1 H), 6.76 (m, 5 H), 5.95 (s, 2 H), 5.04 (d, J=9.86, 1 H), 4.53 (d, J=9.67, 1 H), 4.02 (m, 2 H), 3.78 (s, 3 H), 3.55 (m, 1 H), 3.45 (m, 1 H), 3.34 (,J=9.82, 1 H), 2.66 (m, 2 H), 2.58 (m, 2 H), 2.14 (m, 1 H), 1.56 (m, 2 H), 1.44 (m, 2 H), 1.28 (m, 2 H), 1.11 (m, 2 H), 1.01 (d, J=6.77, 3 H), 0.86 (t, J=7.26, 3 H), 0.81 (t, J=7.37, 3 H). ¹³C NMR (CDCl₃): 174.1, 164.3, 162.8, 157.8, 148.1, 146.8, 141.6, 136.3, 135.0, 133.1, 132.4, 129.6, 121.8, 121.2, 115.5, 112.3, 108.4, 101.1, 67.4, 64.8, 63.6, 60.4, 55.1, 51.5, 38.8, 37.6, 37.4, 32.3, 30.6, 22.3, 18.9, 18.0, 14.2, 14.0, 13.6.

EXAMPLE 22

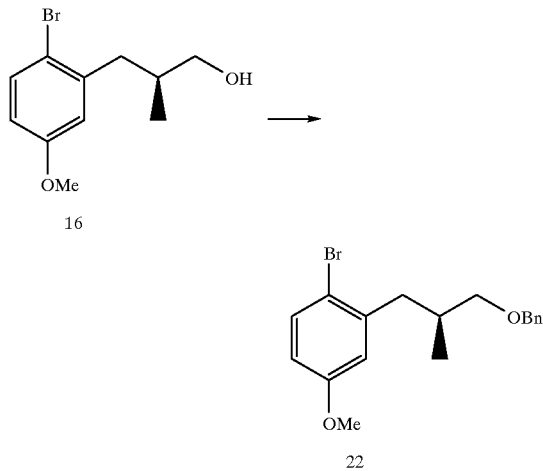

Preparation of 22

To a suspension of 60% NaH (1.25 equ, 7.71g) in THF (450 ml) and DMF (10 ml) was added dropwise a solution of 16 (MW 259.14, 154 mmol, 40.0 g) (Compound 16 was prepared according to the procedure of described in Example 16) in THF (200 ml) below 10° C. Benzylchloride (MW 126.59, 1.1 equ, 21.4 g) was added to the mixture and the mixture was refluxed for 4 h, cooled to room temperature, poured into ice water (500 ml), and extracted with ethyl acetate (1 L). The layers were separated and the aqueous layer was extracted with ethyl acetate. The combined organic layers were washed with dil. HCl, sat. aqueous NaHCO₃, water then brine, dried over anhydrous magnesium sulfate, and evaporated in vacuo. 22 (MW 349.27) was isolated in 98% yield (52.8g) by silica gel chromatography (heptane-ethyl acetate/gradient). ¹H NMR (CDCl₃): 0.96 (d, J=6.60, 3H), 2.20 (m, 1H), 2.70 (m, 2H), 3.37 (m, 2H), 3.73 (s, 3H), 4.52 (s, 2H), 6.63 (dd, J=2.97, 8.91, 1H), 6.75 (d, J=2.97, 1H), 7.37 (m, 5H), 7.41 (d, J=8.91, 1H).

EXAMPLE 23

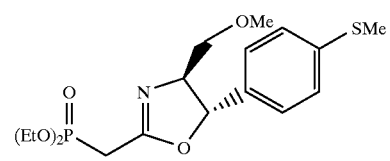

Preparation of 27

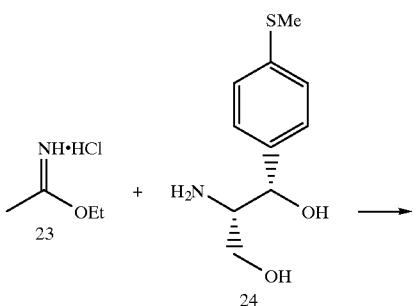

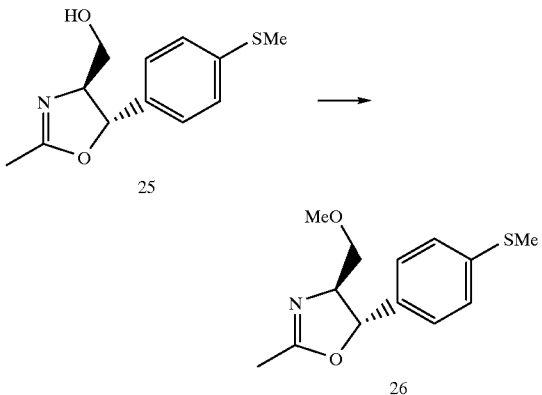

Step A: Preparation of 25

100 g (0.81 mols) of ethylacetimidate hydrochloride, 23 and 173 g (0.81 mols) of (S,S)-thiomicamine, 24 were combined in 1 L of CH₂Cl₂ and stirred at room temperature overnight. The reaction was then quenched with water and extracted with CH₂Cl₂. The organic phase was dried over MgSO₄, filtered, and concentrated under reduced pressure. Recrystallization was accomplished using 700 mL of hot acetonitrile. Crystallization began at about 40° C. The solution was cooled to room temperature (about 20° C.) then cooled to 15° C. The resulting crystals were collected by vacuum filtration and air-dried over night to afford 134.5 g (70%) of the product, compound 25.

Step B: Preparation of 26

51.1 g (215 mmol) of compound 25 from Example 23, Step A were dissolved in 1L of THF and cooled to 0° C. 24.7 g (224 mmol) of sodium t-pentoxide was then added. The mixture was aged at 0–5° C. for about 30 mins. 13.9 mL (224 mmol) of MeI were then added dropwise and the solution allowed to warm to room temperature. After 4 hours, the reaction was quenched with water and extracted with ethylacetate. The organic layer was dried over MgSO$_4$, filtered and concentrated under reduced pressure to yield 54.04 g (100%) of crude product, 26.

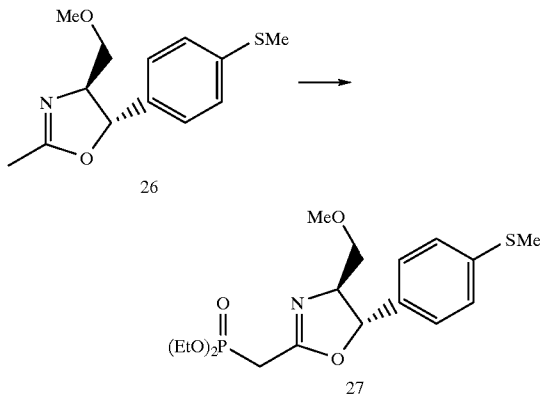

Step C: Preparation of 27

132 mL (946 mmol) of diisopropylamine were dissolved in 200 mL THF and cooled to −21° C. 420 mL (946 mmol) of nBuLi (2.25 M in hexanes) were then added. The mixture was aged at −30 to −45° C. for about 40 minutes. The mixture was then cooled to −78° C. and 108 g (430 mmol) of the product, 26 from Example 23, Step B in 200 mL of THF were added dropwise while maintaining an internal temperature of about −70° C. After an additional 40 minutes, 66.5 mL (460.1 mmol) of diethylchlorophosphate were added neat. The solution was then allowed to warm to −10° C., quenched with water, and extracted with ethylacetate. The organic layer was dried over MgSO$_4$, filtered, and concentrated under reduced pressure to yield 166.11 g (99%) of the crude product, 27.

EXAMPLE 24

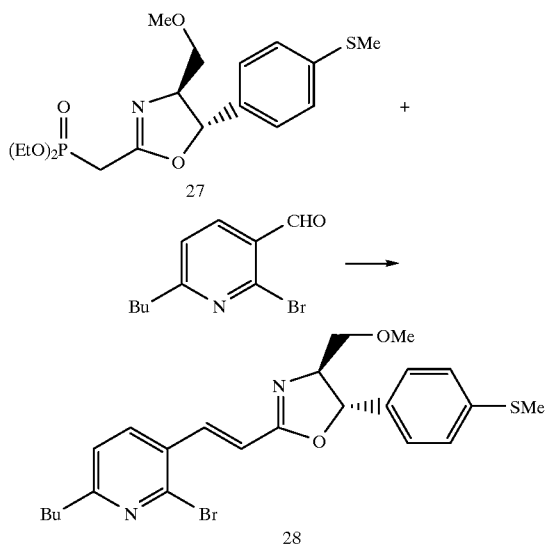

Preparation of 28

83.3 g (215 mmol) of the product, compound 27 from Example 23, Step C were dissolved in 1L THF and cooled to −15° C. 90.3 mL (226 mmol) of nBuLi (2.5 M in hexanes) were then added dropwise while maintaining an internal temperature under 0° C. After 15 minutes, 41.6 g (172 mmol) of 2-bromo-6-butyl-3-pyridinecaboxaldehyde in 70 mL of THF were added dropwise while maintaining an internal temperature between −5° C. and 0° C. After 30 minutes at about −5° C., approximately 13% of the phosphonate ester still remained unreacted. Another 6.7 g (28 mmol) of the aldehyde was then added in THF at 0° C. After another 20 minutes, 4 to 5% of the phosphonate ester remained. An additional 0.27 g (1.12 mmols) of the aldehyde were added. After 30 minutes, the reaction was quenched with water and extracted with ethylacetate. The organic layer was dried over MgSO$_4$, filtered, and concentrated under reduced pressure to yield the crude product, 28.

EXAMPLE 25

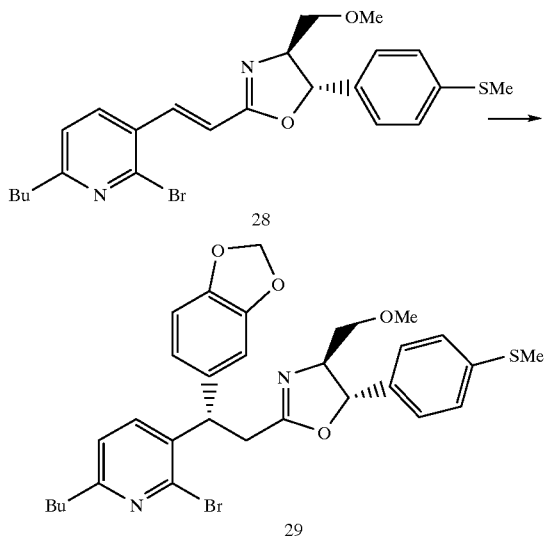

Preparation of 29

107.6 mL (893 mmol) of 4-bromo-1,2-(methylenedioxy) benzene were dissolved in 2L THF and cooled to −78° C. 357 mL (893 mmol) of nBuLi (2.5 M in hexanes) were then added dropwise while maintaining an internal temperature below −72° C. 202 g (425 mmol) of the product from Example 24 in 300 mL THF were added dropwise while maintaining an internal temperature below −70° C. After 30 minutes, the reaction was quenched with methanol at −70° C. and allowed to warm to −10° C. Saturated aqueous NaHCO$_3$ was added and the phases separated. The aqueous layer was filtered through celite and extracted with ethylacetate. The ethylacetate layer was then dried over MgSO$_4$, filtered, and concentrated under reduced pressure to afford 320 g of the crude product, 29. 1H NMR δ (ppm) 0.92 (3H, t); 1.35 (2H,m); 1.68 (2H,m); 2.46 (3H,s); 2.75 (2H,m); centered at 3.05 (2H,dd,dd); centered at 3.4 (2H,dd,dd); 3.34 (3H,s); 3.96 (1H,m); 4.87 (1H, t); 5.18 (1H,d); 5.92 (2H,s); 6.71–6.79 (3H, aromatic multiplet); 6.81–6.88 (2H, aromatic multiplet); 7.09–7.18 (3H, aromatic multiplet), 7.64 (1H,d).

EXAMPLE 26

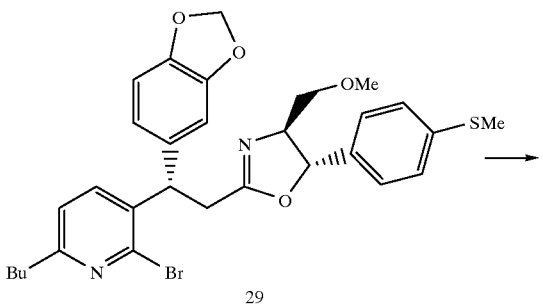

29

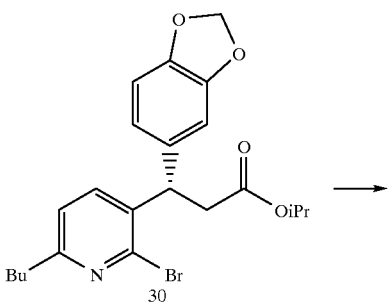

30

Preparation of 30

To a solution of 47.6 g (79.6 mmol) of 29, the product from Example 25 in 200 mL of isopropanol was added 44 mL of concentrated $H_2SO_4$ (18 M). The mixture was then heated to reflux. After 2.5 hours, the mixture was cooled to room temperature and diluted with water. The mixture was then extracted with ethylacetate and washed with a saturated aqueous solution of $NaHCO_3$. The organic phase was concentrated under reduced pressure and the residue dissolved in tert-buytl methyl ether. The ethereal solution was washed with 1N aqueous HCl and with a saturated aqueous solution of $NaHCO_3$. The organic layer was then dried over $MgSO_4$, filtered and concentrated under reduced pressure. The crude product was purified by column chromatography using a solvent gradient of 10:1 hexane/ethylacetate to 5:1 hexane/ethylacetate to afford 25.15 g (70%) of product, 30.

$^1$H NMR δ ( ppm) 0.91 (3H, triplet ); 1.07 (3H, d); 1.13 (3H,d); 1.35 (2H, m); 1.65 (2H,m); 2.71 (2H,m); 2.93 (2H,m); 4.7–4.96 (2H, overlapping multiplets); 5.96 (2H,s); 6.72 (3H, aromatic multiplet); 7.05 (1H,d), 7.43 (1H,d).

EXAMPLE 27

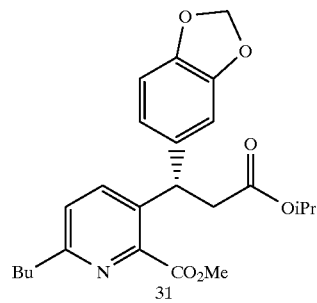

30

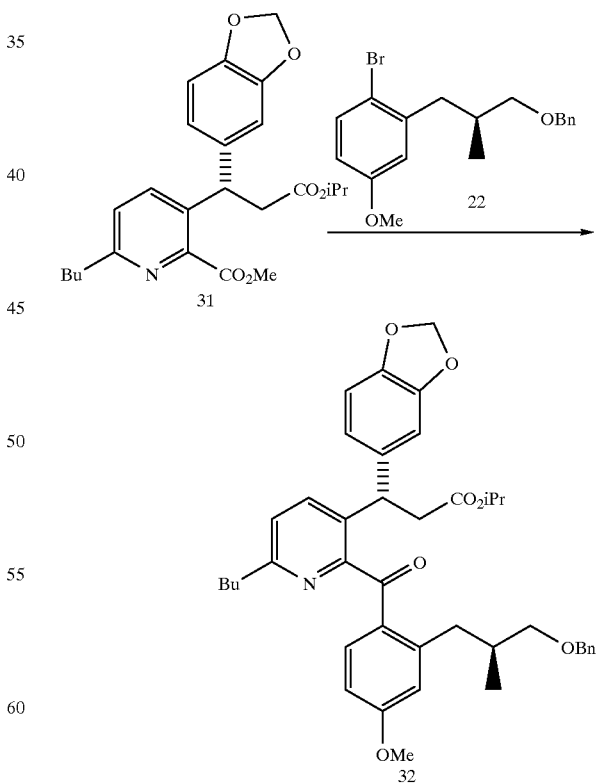

31

Preparation of 31

To a solution of 2 g (3.9 mmol) of 30, the product from Example 26, 66 mg (0.12 mmol) of DPPF (1,1'-bis (diphenylphosphino)-ferrocene) and 67 mg (8 mmol) of $NaHCO_3$ in 20 mL of methanol was added 27 mg (0.12 mmol) of palladium diacetate. The mixture was heated at 70° C. under 40 psi of carbon monoxide for 12 hours. The mixture was then cooled, concentrated under reduced pressure, and partitioned between ethylacetate and water. The aqueous layer was extracted with ethylacetate and the combined organic layers were dried over $MgSO_4$. The organic solvent was removed under reduced pressure to afford 1.56 g (94%) of the crude product, 31.

$^1$H NMR δ ($CDCl_3$, ppm): 0.9(3H,t); 1.06(6H,d); 1.37 (2H,m); 1.66(2H,m); 2.78(2H,m); 2.93(2H,m); 3.94(3H,s); 4.89(1H,m); 5.13(1H,t); 5.88(2H,s); 6.67–6.75(3H, aromatic multiplet); 7.2(1H,d); 7.56(1H,d).

EXAMPLE 28

Preparation of 32

To a cold solution of 22 (see Example 22, MW 349.27, 1.3 equ, 63.76 g) in THF (450 ml) was added n-BuLi (1.7M in hexane, 1.3 equ, 110 ml), maintaining temperature below −70° C., and the mixture was stirred at −78° C. for 10 min. The mixture was added to a solution of 31 (MW 427.50, 0.14 mol, 60.0 g) in THF (450 ml) through cannula below −70° C. The mixture was stirred at −78° C. for 30 min, quenched with water (450 ml), and extracted with ethyl acetate (900 ml). The layers were separated and the aqueous layer was extracted with ethyl acetate. The combined organic layers were washed with water then brine, dried over anhydrous magnesium sulfate, and evaporated in vacuo. 32 (MW 665.82) was isolated in 84% yield (78.4 g) by silica gel chromatography (heptane-ethyl acetate/gradient).

$^1$H NMR (CDCl$_3$): 0.87 (t, J=7.26, 3H), 1.04 (d, J=6.93, 3H), 1.05 (d, J=6.27,6H), 1.26 (m, 2H), 1.62 (m, 2H), 2.29 (m, 1H), 2.71 (t, J=7.59, 2H), 2.92 (J=6.26, 2H), 3.03 (m, 2H), 3.45 (m, 2H), 3.80 (s, 3H), 4.52 (s, 2H), 4.66 (t, J=7.26, 1H), 4.85 (m, 1H), 5.82 (m, 2H), 6.56 (m, 4H), 6.78 (s, 1H), 7.02 (d, J=8.91, 1H), 7.14 (d, J=8.25, 1H), 7.35 (m, 5H), 7.56 (d, J=8.25, 1H).

EXAMPLE 29

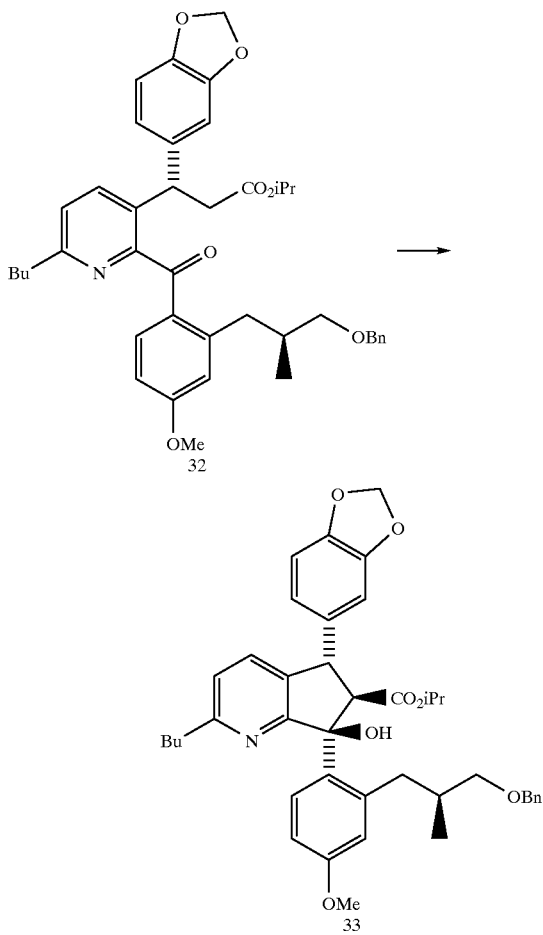

Preparation of 33

To a solution of 32 (MW 665.82, 110 mmol, 73.06 g) in THF (750 ml) was added sodium tert-pentoxide (MW 110.14, 3 equ, 36.35g) at −40° C. The mixture was allowed to warm to 0° C., stirred at 0° C. for 1.5 h, poured into water (1 L), and extracted with ethyl acetate (1 L). The layers were separated and the aqueous layer was extracted with ethyl acetate. The combined organic layers were washed with water then brine, dried over anhydrous magnesium sulfate, and evaporated in vacuo. 33 (MW 665.82) was isolated in 66% yield (48.1 g) by silica gel chromatography (heptane-ethyl acetate/gradient).

$^1$H NMR (CDCl$_3$, ppm): 0.80 (d, J=5.94, 3H), 0.87 (t, J=7.26, 3H), 1.03 (d, J=6.27, 3H), 1.13 (d, J=6.27, 3H), 1.30 (m, 2H), 1.60 (m, 2H), 2.14 (m, 2H), 2.27 (m, 1H), 2.71 (m, 2H), 3.08 (m, 2H), 3.37 (s, 1H), 3.48 (d, J=8.91, 1H), 3.80 (s, 3H), 4.37 and 4,44 (ABq, J=11.5, 2H), 4.91 (d, J=8.91, 1H), 4.99 (m, 1H), 5.92 (s, 2H), 6.65 (d, J=7.92, 1H), 6.76 (m, 4H), 7,05 (d, J=7.92, 1H), 7.28 (m, 6H), 7.71 (d, J=8.54, 1H).

EXAMPLE 30

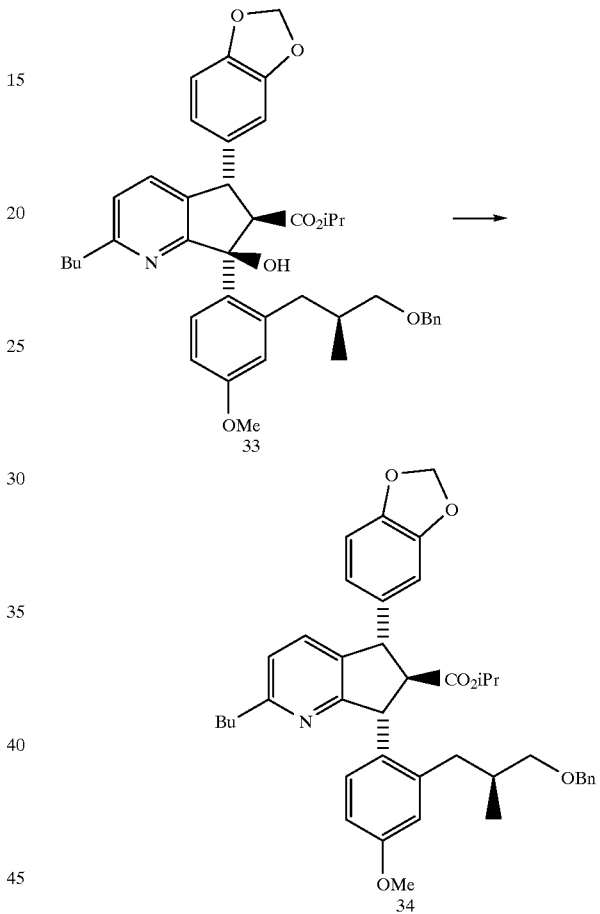

Method A: Preparation of 34

To a predegassed solution of 33 (MW 665.82, 22.8 mmol, 15.2 g) and isopropyl alcohol (5 equ, 8.7 ml) in THF (100 ml) was added SmI$_2$ (0.1 M in THF, 4.8 equ, 1.1 L) under argon atmosphere at room temperature. The mixture was stirred at the same temperature over night, concentrated in vacuo, poured into 0.5N HCl (250 ml), and extracted with ethyl acetate (250 ml). The layers were separated and the aqueous layer was extracted with ethyl acetate. The combined organic layers were washed with water, sat. aqueous NaHCO$_3$, 5% Na$_2$SO$_3$, water then brine, dried over anhydrous magnesium sulfate, and evaporated in vacuo. 34 (MW 649.83) was isolated in quantitative yield (15.1 g) by silica gel chromatography (heptane-ethyl acetate/gradient).

$^1$H NMR (CDCl$_3$, ppm): 0.84 (t, J=7.26, 3H), 1.04 (d, J=6.93, 3H), 1.08 (d, J=6.27, 3H), 1.11 (d, J=6.27, 3H), 1.26 (m, 2H), 1.56 (m, 2H), 2.20 (m, 1H), 2.65 (m, 2H), 2.72 (m, 2H), 3.18 (t, J=9.74, 1H), 3.38 (m, 2H), 3.75 (s, 3H), 4.48 (d, J=8.90 1H), 4.49 (s, 2H), 4.96 (m, 2H), 5.95 (s, 2H), 6.73 (m, 5H), 6.91 (d, J=7.91, 1H), 7.15 (d, J=7.92, 1H), 7.30 (m, 6H).

EXAMPLE 31

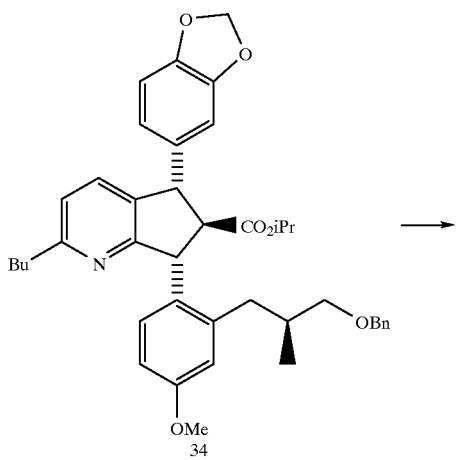
34

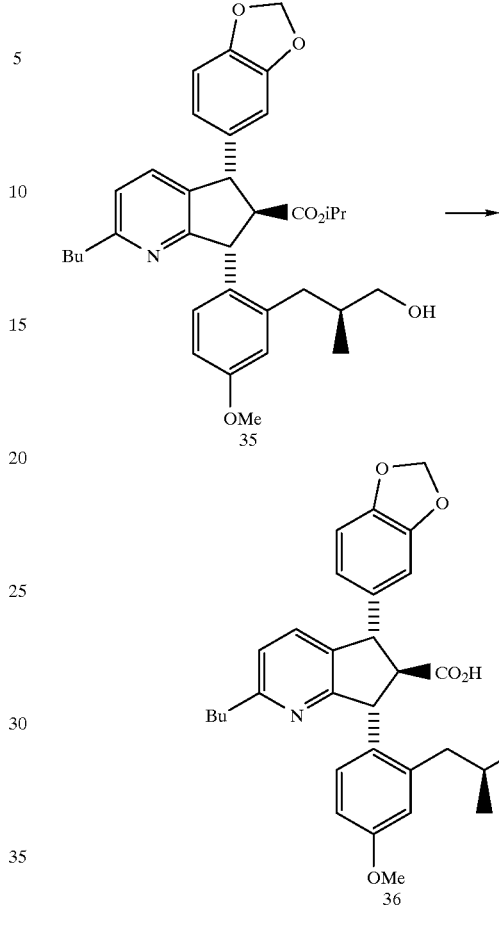

35

Preparation of 35

To a solution of 34 (MW 649.83, 18.5 mmol, 12.0 g) in THF (60 ml) and isopropyl alcohol (60 ml) was added 10% Pd-C (10.5 g), and the mixture was hydrogenated under $H_2$ (3.5 kg/cm2) at 60° C. for 4 h. The catalyst was removed by filtration, and the filtrate was evaporated in vacuo to give 35 (MW 559.70) in 83% yield (8.62 g).

$^1$H NMR (CDCl$_3$, ppm): 0.86 (t, J=7,26, 3H), 1.01 (d, J=6.60, 3H), 1.10 (d, J=6.27, 3H), 1.13 (d, J=6.27, 3H), 1.26 (m, 2H), 1.56 (m, 2H), 2.13 (m, 1H), 2.65 (m, 2H), 2.78 (m, 2H), 3.28 (t, J=9.73, 1H), 3.50 (m, 2H), 3.78 (s, 3H), 4.51 (d, J=9.57, 1H), 4.98 (m, 1H), 5.04 (d, J=10.2, 1H), 5.97 (s, 2H), 6.73 (m, 5H), 6,86 (d, J=8.25, 1H), 6.95 (d, J=7.92, 1H), 7.20 (d, J=7.92, 1H).

EXAMPLE 32

Preparation of 36

To a solution of 35 (NW 559.70, 15.4 mmol, 8.62 g) and TEA (5.7 equ, 12.3 ml) in DMSO (25 ml) was added SO$_3$-PY (MW 159.16, 2.9 equ, 7.05 g) at room temperature. The mixture was stirred for 15 min, poured into water (1 L), and extracted with ethyl acetate (200 ml×3 times). The combined organic layers were washed with 10% citric acid then brine, dried over anhydrous magnesium sulfate, and evaporated in vacuo to give 9.6 g of crude aldehyde.

To a solution of the crude aldehyde and 2-methyl-2-butene (30 ml) in tertbutanol (60 ml) was added a solution of NaClO2 (22.1 mmol, 2.00 g) in 0.5M (1)H 3.3) KH$_2$PO$_4$-H$_3$PO$_4$ buffer (60 ml) at room temperature. The mixture was stirred for 45 min and extracted with ethyl acetate (200 ml). The organic layer was washed with 10% citric acid, water then brine, dried over anhydrous magnesium sulfate, and evaporated in vacuo to give crude mono carboxylic acid.

To a solution of the crude mono carboxylic acid in methanol (40 ml) and dioxane (20 ml) was added 4N NaOH (148 mmol, 37 ml), and the mixture was stirred at 60° C. for 1 h. After cooling, the mixture was diluted with water (50 ml), adjusted to pH 8 with 6N HCl, and washed with ethyl acetate (100 ml). The aqueous layer was acidified to pH 3 with HCl aq, and extracted with ethyl acetate (100 ml×3 times). The combined organic layers were washed with water then brine, dried over anhydrous magnesium sulfate, and evaporated in vacuo. 36 (MW 531.60) was isolated in 48% yield (3.90 g) by silica gel chromatography (CH$_2$Cl$_2$- ethyl acetate/gradient).

$^1$H NMR (CDCl$_3$, ppm): 0.84 (t, J=7.26, 3H), 1.26 (m, 2H), 1.32 (d, J=6.60, 3H),1.49 (m, 2H), 2.67 (m, 3H), 3.14 (m, 2H), 3.59 (t, J=9.57, 1H), 3.75 (s, 3H), 4.58 (d, J=9.57, 1H), 4.99 (d, J=9.56, 1H), 6.00 (s, 2H), 6.70 (d, J=2.97, 1H), 6.78 (s, 1H), 6.83 (m, 3H), 6.94 (d, J=8.90, 1H), 7.06 (d, J=7.91, 1H), 7.33 (d, J=7.91, 1H).

EXAMPLE 33

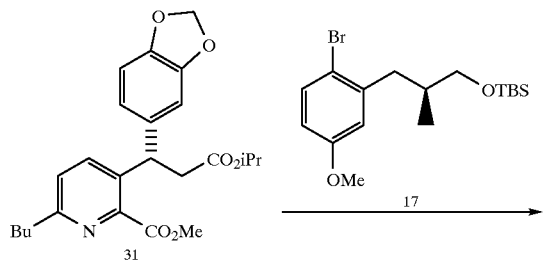

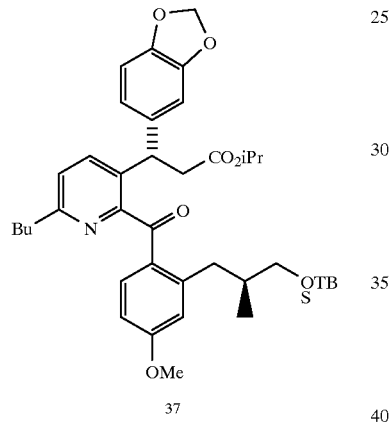

Preparation of 37

To a solution of 2.62 g (7.02 mmol) of the arylbromide 17, Example 17 in 15 mL THF was added 3.3 mL (7.1 mmol) of nBuLi (2.15 M in hexanes) while maintaining an internal temperature below −70° C. After 10 minutes, the solution was transferred via cooled cannula (dry ice) to a solution of the diester, 31 produced in Example 27 in 35 mL of THF. The solution was observed to turn a green-black color. The mixture was stirred for an additional 0.5 hours and then quenched with aqueous NaHCO$_3$. The aqueous layer was extracted with ethylacetate (2×) and the combined organic layers dried over MgSO$_4$. Column chromatography using a 6:1 hexane/ethylacetate solvent system afforded 2.0 g (62%) of product 37 as a yellow oil.

1H NMR δ (CDCl3, ppm): 0.08(6H,s); 0.88(3H,t); 0.92 (9H,s); 0.98(3H,d); 1.05(6H,d); 1.32(2H,m); 1.62(2H,m); 2.11(1H,dd); 2.72(2H,m); 2.93(2H,m); 3.12(1H,dd); 3.51 (1H,dd); 3.62(1H,dd); 3.83(3H,s); 4.66(1H,t); 4.87(1H,m); 5.82(2H,m); 6.5–6.63(4H, aromatic multiplets); 6.81(1H, m); 7.02(1H,d); 7.13(1H,d); 7.58(1H,d).

EXAMPLE 34

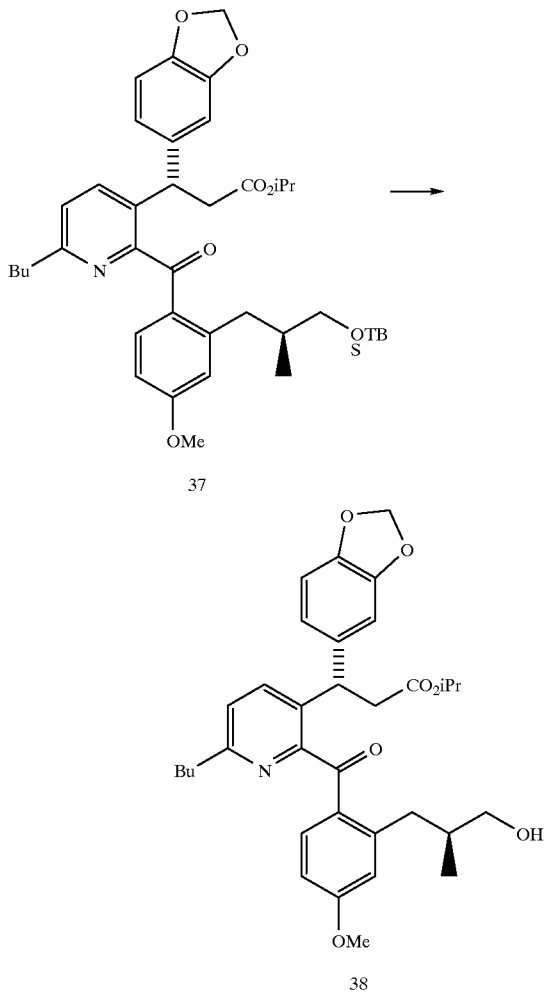

Preparation of 38

To a solution of 0.8 g (1.16 mmol) of the silyl ether, 37 from Example 33 in 20 mL acetonitrile at room temperature was added 0.5 mL og aqueous HF. After 10 minutes, the reaction was quenched with aqueous NaHCO$_3$ and extracted with ethylacetate (2×). The organic layer was dried over MgSO$_4$, filtered, and concentrated under reduced pressure to afford 0.66 g (99%) of the desilylated product, 38 as a yellow foam.

1H NMR (CDCl$_3$, ppm, 300 MHz): δ 0.8 (t, 3H), 0.95 (d, 3H), 1.00 (m, 6H), 1.25 (m, 3H), 1.55 (m, 2H), 2.00 (m, 1H), 2.77 (m, 3H), 2.90 (m, 1H), 3.16 (m, 1H), 3.40 (m, 2H), 3.75 (s, 3H), 4.55 (t, 1H), 4.81 (m, 1H), 5.76 (m, 2H), 6.50 (m, 4H), 6.74 (bs, 1H), 6.89 (d, 1H), 7.43 (d, 1H), 7.85 (d, 1H).

EXAMPLE 35

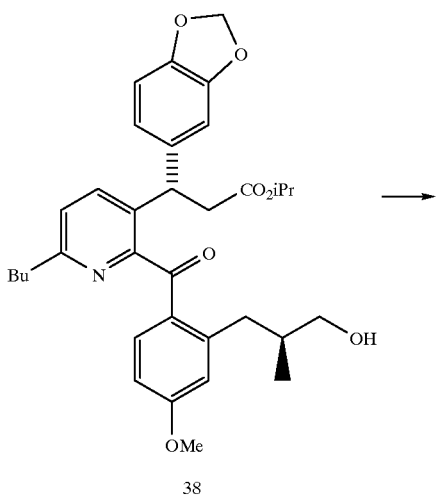

38

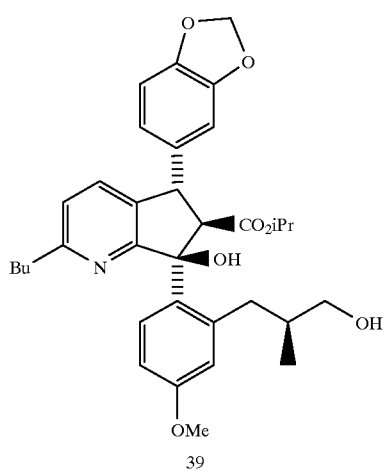

39

Preparation of 39

0.21 g (0.37 mmol) of compound 38, from Example 34 were dissolved in 5 mL THF and cooled to −10° C. 0.12 g (1.1 mmol) of sodium t-pentoxide were then added as a solid and the reaction allowed to warm to room temperature. The reaction was subsequently quenched with 1N aqueous HCl and extracted with ethyl acetate (2×). The organic layer was dried over $MgSO_4$, filtered, and concentrated under reduced pressure to afford 0.21 g (100%) of the crude cyclized product, 39.

$^1$H NMR δ ($CDCl_3$, ppm, 300 MHz): 0.8 (m, 2H), 0.89 (t, 3H), 1.03 (d, 3H), 1.17 (m, 6H), 1.32 (m, 2H), 1.61 (m, 2H), 2.11 (m, 1H), 2.29 (m, 1H), 2.82 (m, 2H), 3.15 (m, 1H), 3.30 (m, 1H), 3.49 (d, 1H), 3.78 (t, 3H), 5.11 (m, 2H), 5.93 (s, 2H), 6.78 (m, 6H), 7.25 (d, 1H), 7.58 (d, 1H).

EXAMPLE 36

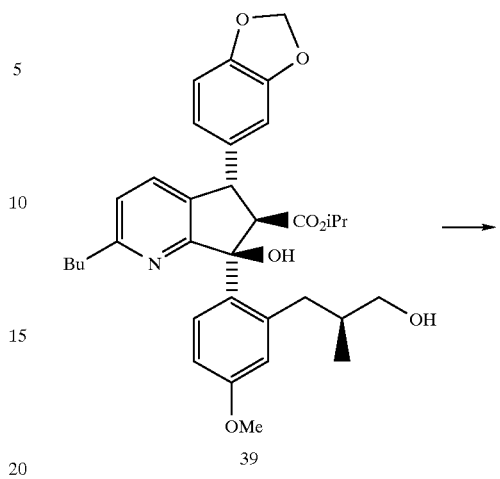

39

40

Preparation of 40

To a solution of dihydroxy ester (4.2 g), 39 in acetone (20 ml) at −15° C. was added Jones reagent (8.4 ml) over a period of 1 h. The reaction was aged 0.5 h, warmed to 0° C. and quenched with water. The phases were separated and the aqueous phase was extracted with MTBE (2×10 ml). The organic phase was concentrated to a tan solid and the crude material was carried directly to the deoxygenation reaction.

$^1$H NMR δ ($CDCl_3$, ppm, 300 MHz): 0.85 (t, 3H), 1.08 (m, 9H), 1.39 (m, 2H), 1.52 (m, 2H), 2.54 (m, 1H), 2.69 (m, 2H), 3.65 (m, 2H), 3.73 (s, 3H), 4.83 (m, 1H), 5.02 (m, 1H), 5.97 (s, 2H), 6.75 (m, 6H), 7.10 (d, 1H), 7.43 (d, 1H).

EXAMPLE 37

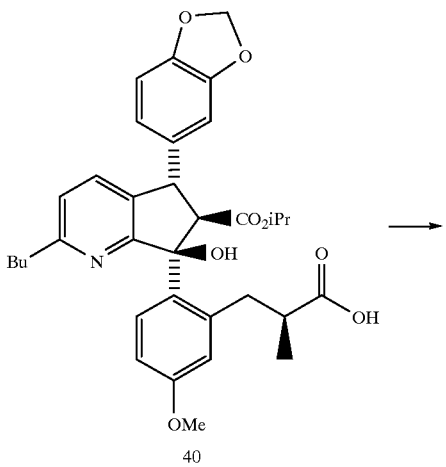

Preparation of 41

To a solution of 1.0 g (1.7 mmol) of compound 40, from Example 36 in 10 mL of tetrahydrofuran (THF) was added 51 mL (5.1 mmol) of $SmI_2$ (0.1 M in THF) at room temperature. After 15 minutes, the reaction was quenched with 1N aqueous HCl and extracted with ethyl acetate twice. The organic layers were dried over $MgSO_4$, filtered and concentrated under reduced pressure to afford 0.98 g (100%) of the crude product 41 as a single diastereomer by $^1H$ NMR.

$^1$H NMR δ ($CDCl_3$, ppm, 300 MHz): 0.85 (t, 3H), 1.05 (d, 3H), 1.13 (m, 2H), 1.15 (d, 3H), 1.3 (d, 3H), 1.5 (m, 2H), 2.65 (m, 2H), 2.95 (m, 2H), 3.35 (dd, 1H), 3.52 (t, 1H), 3.72 (t, 3H), 4.55 (d, 1H), 5.00 (d, 1H), 5.90 (s, 2H), 6.75 (m, 5H), 6.95 (d, 1H), 7.08 (d, 1H), 7.37 (d, 1H).

What is claimed is:

1. A process for the preparation of a compound of formula II:

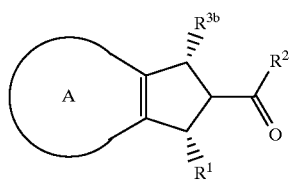

wherein

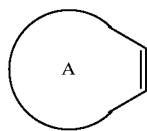

represents:
  a) 5- or 6-membered heterocyclyl containing one, two or three double bonds, but at least one double bond and 1, 2 or 3 heteroatoms selected from O, N and S, the heterocyclyl is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$,
  b) 5- or 6-membered carbocyclyl containing one or two double bonds, but at least one double bond, the carbocyclyl is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$,
  c) aryl, wherein aryl is as defined below,
    $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, are unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_3$–$C_8$ cycloalkyl, $CO(CH_2)_nCH_3$, and $CO(CH_2)_nCH_2N(R^5)_2$,
    aryl is defined as phenyl or naphthyl, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, $CO(CH_2)_nCH_2N(R^5)_2$, and when two substituents are located on adjacent carbons they can join to form a 5- or 6-membered ring with one, two or three heteroatoms selected from O, N, and S, which is unsubstituted or substituted with with one, two or three substituents selected from the group consisting of: H, OH, $CO_2R^6$, Br, Cl, F, I, $CF_3$, $N(R^7)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$,
    n is 0 to 5;
$R^1$ is:
  a) $C_1$–$C_8$ alkyl, $C_2$–$C_8$ alkenyl, $C_2$–$C_8$ alkynyl, $C_3$–$C_8$ cycloalkyl,
  b) aryl, or
  c) heteroaryl;
    heteroaryl is defined as a 5- or 6-membered aromatic ring containing 1, 2 or 3 heteroatoms selected from O, N and S, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$,
$R^2$ is $OR^4$ or $N(R^5)_2$;

$R^{3b}$ is:
a) $C_1$–$C_8$ alkyl,
b) aryl, or
c) heteroaryl;
$R^4$ is $C_1$–$C_8$ alkyl; and
$R^5$ is: H, $C_1$–$C_8$ alkyl, or aryl,
comprising reacting a compound of formula I

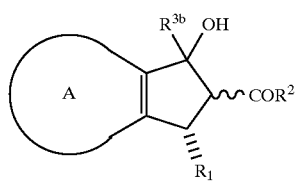

with a reducing agent and optionally an acid in a solvent at a temperature range of about −78° C. to about 100° C.

2. The process as recited in claim 1, wherein the reducing agent is selected from the group consisting of: a hydride, a borane, a $C_5$–$C_6$ cycloalkene with a transition metal catalyst, $H_2$ with a transition metal catalyst and $SmI_2$.

3. The process as recited in claim 2, wherein the acid is a Lewis acid, when the reducing agent is a hydride, a borane or a $C_5$–$C_6$ cycloalkene with a transition metal catalyst; a protic acid, when the reducing agent is $H_2$ with a transition metal catalyst; or is absent when the reducing agent is $SmI_2$.

4. The process as recited in claim 3, wherein the solvent is an aprotic solvent, when the acid is a Lewis acid and the reducing agent is a hydride, a borane or a $C_5$–$C_6$ cycloalkene with a transition metal catalyst; a protic solvent, when the acid is a protic acid and the reducing agent is $H_2$ with a transition metal catalyst; or a solvent system consisting a protic solvent in combination with aprotic solvent.

5. The process as recited in claim 4, wherein the temperature range is about −78° C. to about 20° C., when the acid is a Lewis acid and the reducing agent is a hydride or a borane.

6. The process as recited in claim 4, wherein the temperature range is about 0° C. to 100° C., when the acid is a Lewis acid or a protic acid and the reducing agent is a $C_5$–$C_6$ cycloalkene with a transition metal catalyst or $H_2$ with a transition metal catalyst.

7. The process as recited in claim 4, wherein the temperature range is about 0° C. to 30° C., when the reducing agent is $SmI_2$.

8. The process as recited in claim 5, wherein the aprotic solvent selected from the group consisting of: tetrahydrofuran, diethyl ether, methyl t-butyl ether, dioxane, $CH_2Cl_2$, $CHCl_3$, nitromethane, toluene, and dichlorobenzene.

9. The process as recited in claim 6, wherein the protic solvent selected from the group consisting of: ethanol, methanol, and isopropanol.

10. The process as recited in claim 7, wherein the solvent system consists of a protic solvent selected from the group consisting of methanol, ethanol or isopropanol and an aprotic solvent selected from the group consisting of: tetrahydrofuran, diethyl ether, methyl t-butyl ether or dioxane.

11. The process as recited in claim 7, wherein the Lewis acid is selected from the group consisting of: $TiCl_4$, $BF_3$, $BCl_3$, $SnCl_4$, $AlCl_3$, and $TiCl_2(OiPr)_2$.

12. The process as recited in claim 9, wherein the temperature range is about −20° C. to about 10° C., when the reducing agent is a hydride or a borane.

13. The process as recited in claim 7, wherein the protic acid is selected from the group consisting of: trifluoroacetic acid, HCl, and $H_2SO_4$.

14. The process as recited in claim 10, wherein the hydride is selected from the group consisting of: $R_3SiH$, $R_2SiH_2$, wherein R is $C_1$–$C_8$ alkyl or aryl, and $NaBH_4$.

15. The process as recited in claim 10, wherein the borane is selected from the group consisting of: $BH_3.NHMe_2$, $BH_3.SMe_2$, $BH_3$.pyridine, and $BH_3.THF$.

16. The process as recited in claim 9, wherein the reducing agent is a $C_5$–$C_6$ cycloalkene with a transition metal catalyst selected from cyclohexene or cyclohexadiene with Pd/C, Pt-C, Rh/Al or Raney Ni.

17. The process as recited in claim 14, wherein the temperature range is about 0° C. to about 40° C.

18. The process as recited in claim 12, wherein the $H_2$/transition metal catalyst is selected from the group consisting of: Pd-C, Pt-C, Rh/Al and Raney Ni.

19. The process as recited in claim 16, wherein the temperature range is about 0° C. to about 40° C.

20. The process as recited in claim 12, wherein the hydride is $R_3SiH$, the Lewis acid is $TiCl_4$ the aprotic solvent is nitromethane and the temperature range is about −5° C. to about 5° C.

21. A process for the preparation of a compound of formula:

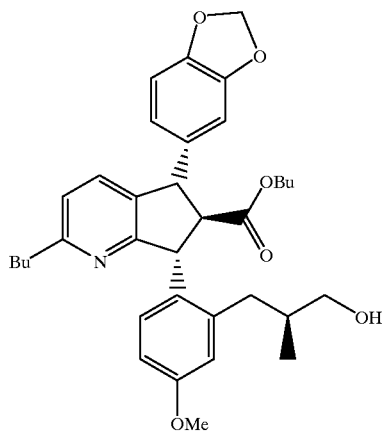

comprising reacting the tertiary alcohol

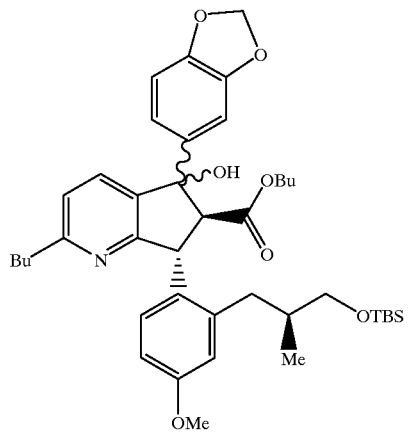

in nitromethane with $Et_3SiH$ and $TiCl_4$ at about −5° C. to about 5° C.

22. A process for the preparation of a compound of formula:
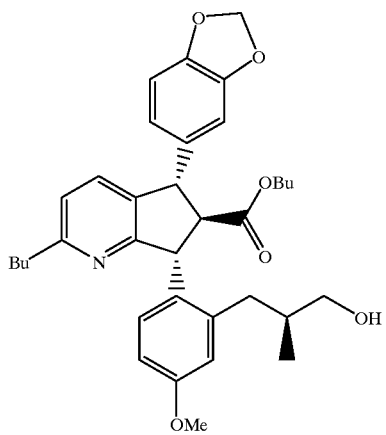
comprising reacting the tertiary alcohol
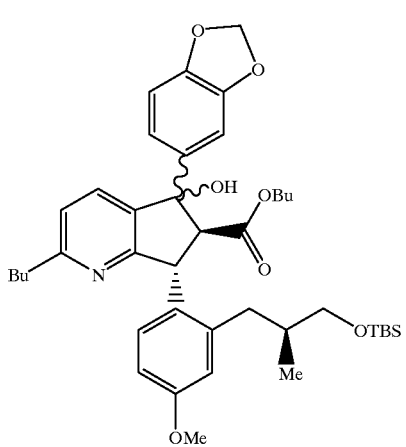
in a solution of isopropyl alcohol and tetrahydrofuran with SmI$_2$ at about 10°–30° C.
23. A process for the preparation of a compound of formula:
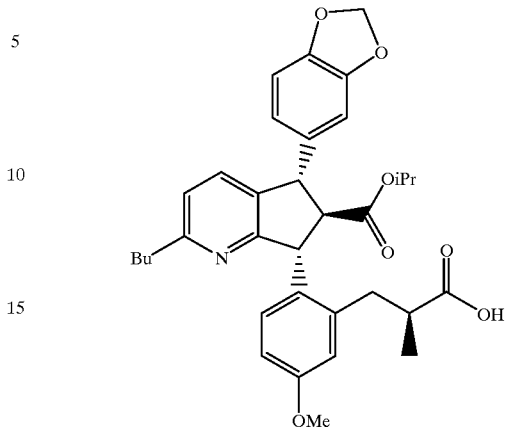
comprising reacting the tertiary alcohol
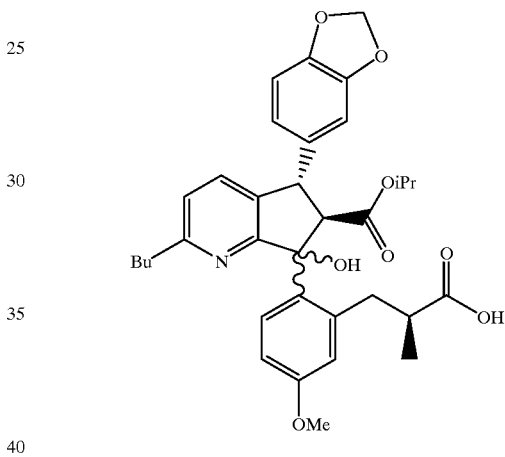
in a solution of isopropyl alcohol and tetrahydrofuran with SmI$_2$ at about 10°–30° C.
* * * * *